US012802791B2

(12) United States Patent
Wu

(10) Patent No.: US 12,802,791 B2
(45) Date of Patent: Nov. 17, 2026

(54) CDA ENTITY DETECTION AND RESOLUTION PIPELINE

(71) Applicant: Oracle International Corporation, Redwood Shores, CA (US)

(72) Inventor: Yuanxu Wu, Sunnyvale, CA (US)

(73) Assignee: Orade International Corporation, Redwood Shores, CA (US)

( * ) Notice: Subject to any disclaimer, the term of this patent is extended or adjusted under 35 U.S.C. 154(b) by 125 days.

(21) Appl. No.: 18/885,346

(22) Filed: Sep. 13, 2024

(65) Prior Publication Data

US 2025/0094710 A1 Mar. 20, 2025

Related U.S. Application Data

(60) Provisional application No. 63/583,234, filed on Sep. 15, 2023.

(51) Int. Cl.

| | |
|---|---|
| ***G16H 10/60*** | (2018.01) |
| ***G06F 40/284*** | (2020.01) |
| ***G06F 40/295*** | (2020.01) |
| ***G16H 20/10*** | (2018.01) |
| ***G16H 80/00*** | (2018.01) |

(52) U.S. Cl.
CPC ........... *G16H 10/60* (2018.01); *G06F 40/284* (2020.01); *G06F 40/295* (2020.01); *G16H 20/10* (2018.01); *G16H 80/00* (2018.01)

(58) Field of Classification Search
CPC ........ G16H 10/60; G06F 40/20; G06F 40/205
See application file for complete search history.

(56) References Cited

U.S. PATENT DOCUMENTS

| | | | | |
|---|---|---|---|---|
| 10,373,711 | B2 * | 8/2019 | D'Souza | G06Q 30/04 |
| 2015/0356198 | A1 * | 12/2015 | D'Souza | G16H 50/20 705/2 |
| 2019/0198141 | A1 * | 6/2019 | Bacon | G16H 10/60 |
| 2022/0198150 | A1 * | 6/2022 | Karres | G16H 10/20 |
| 2024/0153633 | A1 * | 5/2024 | Palaniappan | G06N 3/088 |
| 2026/0011433 | A1 * | 1/2026 | Bergmann | G16H 40/20 |

* cited by examiner

*Primary Examiner* — Daniel Abebe
(74) *Attorney, Agent, or Firm* — Kilpatrick Townsend & Stockton LLP

(57) ABSTRACT

The techniques described herein provide a novel clinical digital assistant (CDA) processing pipeline enabling medical entity detection and resolution that works against various EHRs and with different ontologies (e.g., medical coding systems). In some embodiments, the processing pipeline may involve two machine-learning models that can perform named entity recognition on the natural language utterance to identify medical entities that are associated with different medical entity types, and link the medical entities to medical codes of standard medical coding systems. A FHIR-compliance data structure may be generated using the identified medical codes, their associated medical coding systems, the identified medical entities, and their associated medical entity types.

30 Claims, 12 Drawing Sheets

CDA ENTITY DETECTION AND RESOLUTION PIPELINE

CROSS-REFERENCES TO RELATED APPLICATIONS

This application is a non-provisional of and claims the benefit and priority under 35 U.S.C. 119(e) of U.S. Provisional Application No. 63/583,234, titled "CLINICAL DIGITAL ASSISTANT," filed on Sep. 15, 2023, which is incorporated herein by reference in its entirety for all purposes.

BACKGROUND

Clinical environments such as healthcare facilities often include different healthcare providers working together and communicating with one another to treat patients. Documenting patient encounters, capturing information conveyed during those encounters and/or pertaining to events occurring before and/or after the encounters, populating patient records such as electronic health records, and healthcare practice management are integral parts of the practice of many healthcare providers and important to ensuring high-quality healthcare. Traditional means for performing tasks associated with providing healthcare often involve several different devices such as listening devices, portable electronic devices, workstations, and the like and end users who are equipped with the training, knowledge, experience, and skills to properly utilize these devices and participate in the healthcare process. Relying on different devices and qualified end users to perform clinical tasks is cumbersome, time and resource intensive, costly, and reduces efficiencies, which may lead to lower-quality healthcare.

BRIEF SUMMARY

Techniques disclosed herein pertain to generating electronic health records (EHR). More specifically, techniques are disclosed for generating electronic health records in a data structure in compliance with Fast Healthcare Interoperability Resources (FHIR) standard for exchanging health care information electronically.

In some embodiments, a method includes accessing a natural language utterance comprising a plurality of tokens, wherein a first token of the plurality of tokens corresponds to a first medical entity; performing an entity analysis on the natural language utterance by: using a first machine-learning model to assign a first class label to the first token, wherein the first class label is selected from a plurality of class labels and associated with the first medical entity, and using a second machine-learning model to link the first medical entity to a first medical code, wherein the first medical code is included in a first medical coding system that is associated with the first medical entity; generating a data structure comprising the first token, the first class label, and the first medical code; and storing the data structure in a database associated with an electronic health record (EHR) system.

In some embodiments, the method further includes identifying an intent from the natural language utterance.

In some embodiments, the identified intent is a query for medical-related information.

In some embodiments, each class label of the plurality of class labels corresponds to a respective medical entity type of a plurality of medical entity types; the first medical coding system is included in a group of medical coding systems; and using the second machine-learning model to link the first medical entity to the first medical code comprises: using the second machine-learning model to associate the first medical entity with a first medical entity type of the plurality of medical entity types; and selecting the first medical coding system from the group of medical coding systems based on the first medical entity type.

In some embodiments, the first medical coding system is Systematized Nomenclature of Medicine—Clinical Terms (SNOMED CT), Prescription Normalization (RxNORM), Logical Observation Identifiers Names and Codes (LOINC), or International Classification of Diseases (ICD-10).

In some embodiments, the data structure is in compliance with Fast Healthcare Interoperability Resources (FHIR) standard.

In some embodiments, the method further includes using the data structure to generate a response to the natural language utterance.

In some embodiments, the method further includes assigning a higher priority to the first token of the plurality of tokens than a second token of the plurality of tokens, wherein the second token corresponds to a non-medical entity.

In some embodiments, the first machine-learning model is trained based on a supervised learning technique using training data including a plurality of training natural language utterances, wherein each training natural language utterance is labeled with one or more medical entities.

In some embodiments, the second machine-learning model is trained based on an unsupervised learning technique using training data including data structures including a plurality of medical entities, a plurality of medical entity types associated with the plurality of medical entities, and a plurality of medical code systems associated with the medical entity types.

Some embodiments include a system that includes one or more processing systems and one or more computer-readable media storing instructions which, when executed by the one or more processing systems, cause the system to perform part or all of the operations and/or methods disclosed herein.

Some embodiments include one or more non-transitory computer-readable media storing instructions which, when executed by one or more processing systems, cause a system to perform part or all of the operations and/or methods disclosed herein.

The techniques described above and below may be implemented in a number of ways and in a number of contexts. Several example implementations and contexts are provided with reference to the following figures, as described below in more detail. However, the following implementations and contexts are but a few of many.

DETAILED DESCRIPTION

Figure 1:
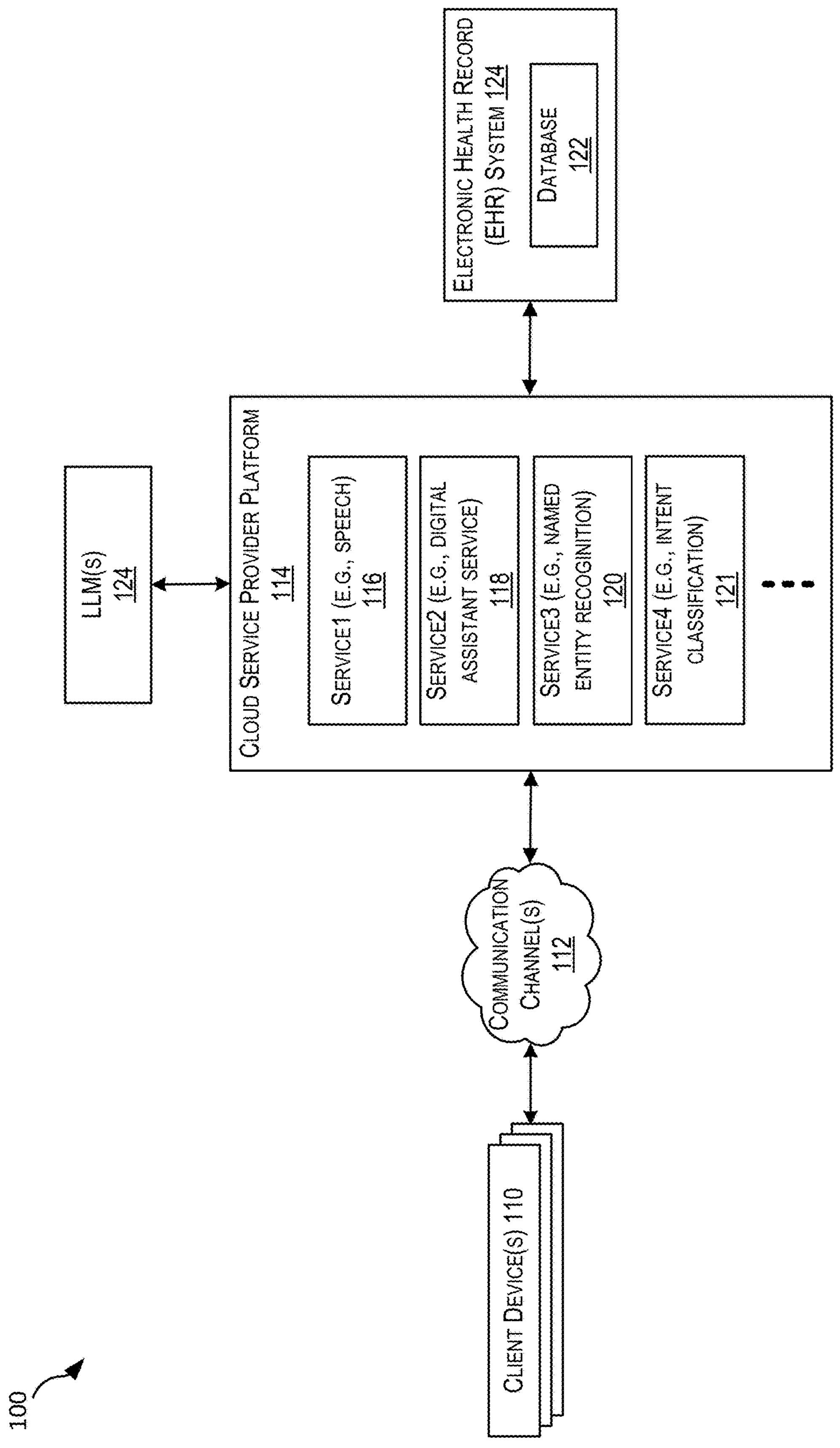
FIG. 1 is an example of a healthcare environment 100 that includes capabilities for providing various services to healthcare providers to facilitate care and management of their patient populations, according to certain embodiments.

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

Digital assistants have been employed in clinical environments to facilitate healthcare providers and practitioners in performing their daily tasks and treating patients. Many digital assistants are equipped with speech, language, and chat functionality so that an end user can interact and converse with the digital assistant using language to get information and/or facilitate a task. These digital assistants are often used in many different contexts (e.g., hospitals, specialist offices, common areas) by many different healthcare providers and practitioners and for many different patients. Additionally, these digital assistants often interface with various electronic health record (EHR) systems.

Typically, to facilitate such functionality, these digital assistants often include a natural language understanding pipeline that functions to understand text or speech utterances made by the end user, such as a doctor, and take some kind of action in response to it. For example, the digital assistant can listen to patient-doctor encounters and generate notes documenting the encounter, and/or a healthcare provider can dictate to the digital assistant, which in turn can populate an EHR for the patient. The natural language understanding pipeline often uses machine learning models to determine the end user's intent by inputting the voice or text into the respective machine learning models. A speech model translates the voice to text (e.g., ASR), and a language model resolves the end user's intent from the text (e.g., by classifying entities and classifying intents).

The language model may process a transcript by extracting entities and classifying the end user's intent based on the entities and the context of those entities within the utterance. In a clinical setting, the entities often include medical entities such as the symptoms, medications, vital signs, and the like. Additionally, EHR systems often use medical entities that are specific to the respective EHR system. For example, one particular EHR may use the Fast Healthcare Interoperability Resources (FHIR) standard for exchanging health care information electronically and another EHR may use the Health Level 7 (HL7) or Clinical Document Architecture (CCDA) formats. FHIR may refer to a standard for exchanging healthcare information electronically between different systems, which may utilize modern web technologies such as RESTful APIs and JSON/XML format to facilitate the exchange.

Due to the variability of medical entities across clinical settings, in different geographic regions, and the different standards, recognizing these entities in end user utterances is challenging. As such, it becomes challenging to determine the end user's intent when an utterance includes one or more of these entities, which further complicates downstream tasks such as fulfilling medical orders, populating EHR for patients, and the like. Additionally, the medication order process typically uses form filling, which may be inefficient and error-prone. For example, the medication to be ordered may be written on a physician's order form (becoming part of a patient's medical record), and then be delivered to a pharmacy to review the order. The ordering process may involve many parties, and back-and-forth communication to finalize the order. Thus, there is a need to address these challenges and others. Embodiments described herein address these and other problems, individually and collectively.

The techniques described herein provide a novel clinical digital assistant (CDA) processing pipeline enabling medical entity detection and resolution that works against various EHRs and with different ontologies (e.g., medical coding systems). In some embodiments, the processing pipeline may involve two machine-learning models that can perform named entity recognition on the natural language utterance to identify medical entities that are associated with different medical entity types, and link the medical entities to medical codes of standard medical coding systems. A FHIR-compliance data structure may be generated using the identified medical codes, their associated medical coding systems, the identified medical entities, and their associated medical entity types.

For example, a healthcare provider (e.g., a doctor) may have a query (or utterance), "Show me Mary Alice's (a patient's name) recent visit, including her blood pressure." The processing pipeline may identify the intent of the end-user, and extract entities, such as the patient's name "Mary Alice" and "blood pressure." Based on the extracted medical entity (e.g., blood pressure) that is associated with medical entity type "vitals, the pipeline may identify the SNOMED CT coding system specialized in the medical entity type. A medical code in the SNOMED CT coding system may be found and linked to the medical entity (e.g., blood pressure). The FHIR-compliance data structure may be generated based on the above information, and used to obtain Mary Alice's record containing the measurement information (e.g., blood pressure) from an EHR system.

In some embodiments, an additional medication order pipeline may be used to facilitate medication orders by identifying the medication ordering intent from a natural language utterance, and using the FHIR-compliance data structure to generate medication order information to fulfill medication orders through an EHR system. The medication order information may be a concise search phrase containing the medical entities extracted from the data structure, or converted EHR system-specific medical codes based on the standard medical codes in the data structure.

For example, a natural language utterance may include, "Please order Tylenol to help alleviate headache using oral tablets, and let's start with 200 milligrams." The medication order pipeline can use the medical entities in the FHIR-compliance data structure generated by the medical entity detection and resolution pipeline to form a concise search phrase (e.g., "Tylenol 200 mg oral tablets") or convert the RxNORM medical codes in the data structure to EHR system-specific medical codes.

Embodiments of the present disclosure provide a number of advantages/benefits. The generated FHIR-compliance data structure that includes the standard medical codes can be stored in EHR systems, and used to retrieve patient records accurately and consistently because such standard medical codes can avoid using unprecise terms in user's utterances. Additionally, the medication order pipeline provides medication order information that is flexible and adaptable to different EHR systems, while achieving automatic, efficient, and accurate medication orders.

Introduction

Artificial intelligence techniques have broad applicability. For example, a digital assistant is an artificial intelligent driven interface that helps users accomplish a variety of tasks in natural language conversations. For each digital assistant, a customer may assemble one or more skills. Skills (also described herein as chatbots, bots, or skill bots) are individual bots that are focused on specific types of tasks, such as tracking inventory, submitting time cards, and creating expense reports. When an end user engages with the digital assistant, the digital assistant evaluates the end user input and routes the conversation to and from the appropriate chatbot. The digital assistant can be made available to end users through a variety of channels such as FACEBOOK® Messenger, SKYPE MOBILE® messenger, or a Short Message Service (SMS). Channels carry the chat back and forth from end users on various messaging platforms to the digital assistant and its various chatbots. The channels may also support user agent escalation, event-initiated conversations, and testing.

Intents allow artificial intelligence-based technology such as a chatbot to understand what the user wants the chatbot to do. Intents are the user's intention communicated to the chatbot via user requests and statements, which are also referred to as utterances or natural language utterances (e.g., get account balance, make a purchase, etc.). As used herein, an utterance or a message may refer to a set of words (e.g., one or more sentences) exchanged during a conversation with a chatbot. Intents may be created by providing a name that illustrates some user action (e.g., order a pizza) and compiling a set of real-life user statements, or utterances that are commonly associated with triggering the action. Because the chatbot's cognition is derived from these intents, each intent may be created from a data set that is robust (one to two dozen utterances) and varied, so that the chatbot may interpret ambiguous user input. A rich set of utterances enables a chatbot to understand what the user wants when it receives messages like "Forget this order!" or "Cancel delivery!"—messages that mean the same thing, but are expressed differently. Collectively, the intents, and the utterances that belong to them, make up a training corpus for the chatbot. By training a model with the corpus, a customer may essentially turn that model into a reference tool for resolving end user input to a single intent. A customer can improve the acuity of the chatbot's cognition through rounds of intent testing and intent training.

FIG. 1 is an example of a healthcare environment 100 that includes capabilities for providing various services to healthcare providers to facilitate care and management of their patient populations, according to certain embodiments. The term healthcare provider generally refers to healthcare practitioners and professionals including, but not limited to: physicians (e.g., general practitioners, specialists, surgeons, etc.); nurse professionals (e.g., nurse practitioners, physician assistants, nursing staff, registered nurses, licensed practical nurses, etc.); other professionals (e.g., pharmacists, therapists, technicians, technologists, pathologists, dietitians, nutritionists, emergency medical technicians, psychiatrists, psychologists, counselors, dentists, orthodontists, hygienists, etc.).

For the purpose of this disclosure, a healthcare environment may refer to the overall setting in which healthcare services are provided, such as hospitals, clinics, long-term care facilities, policy, procedure, and how care is delivered. A clinic environment may refer to the settings where patient care and clinical procedures are performed. In some embodiments, the terms healthcare environment and clinical environment may be used interchangeably.

The healthcare environment 100 includes a cloud service provider platform 114 that includes capabilities for providing various services to subscribers (e.g., end-users) of the cloud service provider platform 114. The end-users (e.g., clinics such as doctors and nurses) may utilize the various services provided by the cloud service provider platform 114 to perform various functions involving the treatment, care, observation, and so on of patients. For instance, in the healthcare environment 100, the end-users can utilize the functionality provided by the services to view, edit, or manage a patient's electronic health record, perform administrative tasks such as scheduling appointments, manage patient populations, provide customer service to facilitate operation of the healthcare environment 100 and so on.

As shown in FIG. 1, the environment 100 includes one or more client devices 110 (hereinafter "client devices 110"), one or more communication channels 112 (hereinafter "communication channels"), a cloud service provider platform 114 (hereinafter "platform 114"), one or more databases 122 (hereinafter "databases 122"), and one or more LLMs 124 (hereinafter "LLMs"). The platform 114, which can be included as part of a cloud infrastructure of a cloud service provider (e.g., Oracle Cloud Infrastructure or OCI), can be configured to communicate with, send data and information to, and receive data and information from the client devices 110 via the communication channels 112. Additionally, the platform 114 can be configured to access and/or call the databases 122 and the LLMs 124 to obtain and/or receive data and information from the databases 122 and the LLMs 124. Data and information received from the client devices 110, the databases 122, and the LLMs 124 can be used by the platform 114 to execute tasks and perform services. While FIG. 1 shows the databases 112 and the LLMs 124 as being separate from the platform 114, this is not intended to be limiting, and one or more of the databases 112 and/or one or more of the LLMs 124 can be included as part of the platform 114 and/or the cloud infrastructure in which the platform 114 is included. In some embodiments, the databases 112 may be part of an electronic health record (EHR) system 124, which may collect and store information relevant to the observation, care, treatment, and/or management of patients, and so on.

Each client device included in the client devices 110 can be any kind of electronic device that is capable of: executing applications; presenting information textually, graphically, and audibly such as via a display and a speaker; collecting information via one or more sensing elements such as image sensors, microphones, tactile sensors, touchscreen displays, and the like; connecting to a communication channel such as the communication channels 112 or a network such as a wireless network, wired network, a public network, a private network, and the like, to send and receive data and information; and/or storing data and information locally in one or more storage mediums of the electronic device and/or in one or more locations that are remote from the electronic device such as a cloud-based storage system, the platform 114, and/or the databases 112. Examples of electronic devices include, but are not limited to, mobile phones, desktop computers, portable computing devices, computers, workstations, laptop computers, tablet computers, and the like.

In some implementations, an application can be installed on, executed on, and/or accessed by a client device included in the client devices 110. The application and/or a user interface of the application can be utilized or interacted with (e.g., by an end user) to access, utilize, and/or interact with one or more services provided by the platform 114. The client device can be configured to receive multiple forms of input such as touch, text, voice, and the like, and the application can be configured to transform that input into one or more messages which can be transmitted or streamed to the platform 114 using one or more communication channels of the communication channels 112. Additionally, the client device can be configured to receive messages, data, and information from platform 114 using one or more communication channels of the communication channels 112, and the application can be configured to present and/or render the received messages, data, and information in one or more user interfaces of the application.

Each communication channel included in the communication channels 112 can be any kind of communication channel that is capable of facilitating communication and the transfer of data and/or information between one or more entities such as the client devices 110, the platform 114, the databases 112, and the LLMs 124. Examples of communication channels include, but are not limited to, public networks, private networks, the Internet, wireless networks, wired networks, local area networks, wide area networks, and the like. The communication channels 112 can be configured to facilitate data and/or information streaming between and among the one or more entities. In some implementations, data and/or information can be streamed using one or more messages and according to one or more protocols. Each of the one or more messages can be a variable-length message, and each communication channel included in the communication channel 112 can include a stream orchestration layer that can receive the variable length message in accordance with a predefined interface, such as an interface defined using an interface description language like AsyncAPI. Each of the variable-length messages can include context information that can be used to determine the route or routes for the variable-length message as well as a text or binary payload of arbitrary length. Each of the routes can be configured using a polyglot stream orchestration language that is agnostic to the details of the underlying implementation of the routing tasks and destinations.

Each database included in the databases 112 can be any kind of database that is capable of storing data and/or information and managing data and/or information. Data and/or information stored by each database can include data and/or information generated by, provided by, and/or otherwise obtained by the platform 114. Additionally, or alternatively, data and/or information stored and/or managed by each database can include data and/or information generated by, provided by, and/or otherwise obtained by other sources such as the client devices 110 and/or LLMs 124. One or more databases that are included in the databases 112 can be part of a platform for storing and managing healthcare information such as electronic health records for patients, electronic records of healthcare providers, and the like, and can store and manage electronic health records for patients of healthcare providers. An example platform is the Oracle Health Millenium Platform. Additionally, one or more databases included in the databases 112 can be provided by, managed by, and/or otherwise included as part of a cloud infrastructure of a cloud service provider (e.g., Oracle Cloud Infrastructure or OCI). Data and/or information stored and/or managed by the databases 112 can be accessed using one or more application programming interfaces (APIs) of the databases 112.

The platform 114 can be configured to include various capabilities and provide various services to subscribers (e.g., end users) of the various services. In some implementations, in the case of an end user or subscriber being a healthcare provider, the healthcare provider can utilize the various services to facilitate the observation, care, treatment, management, and so on of their patient populations. For example, a healthcare provider can utilize the functionality provided by the various services provided by the platform 114 to examine or treat a patient; view, edit, or manage a patient's electronic health record; perform administrative tasks such as scheduling appointments, managing patient populations, providing customer service to facilitate operation of a healthcare environment in which the healthcare provider practices, and so on.

In some implementations, the services provided by the platform 114 can include, but are not limited to, service 1 116 (e.g., a speech service), service 2 118 (e.g., a digital assistant service), service 3 120 (e.g., name entity recognition (NER) service, and service 4 121 (e.g., intent classification service). The speech service 116 can be configured to convert audio into text, such as a text transcript. For example, the speech service 116 can convert an audio recording of a conversation between a healthcare provider and their patient into a text transcript of the conversation. To convert audio into text, the speech service 116 can utilize one or more machine-learning models, such as an automatic speech recognition (ASR) model. In the case that the audio is streamed to the platform 114 in the form of messages (as described above) with each message including a portion of the audio (e.g., a one-second segment of the audio), in some implementations, the platform 114 and/or the speech service 116 can be configured to aggregate and combine all of the messages pertaining to the audio (e.g., all of the messages pertaining to a conversation) into audio data or an audio file prior to converting the audio data or audio file into text or a text transcript. In other implementations, the platform 114 and/or the speech service 116 can be configured to convert audio into text or a text transcript as the audio is received by the platform 114 and/or the speech service 116. The text or text transcript generated by the speech service 116 can be stored within the platform 114 and/or in another location, such as in one or more databases of the databases 122, where it can be accessed by the platform 114 and/or one or more other services of the platform 114 such as the digital assistant service 118 and/or the name entity recognition (NER) service 120. Additionally, or alternatively, the text or text transcript generated by the speech service 116 can be provided to one or more other services of the platform 114, such as the digital assistant service 118 and/or the NER service 120.

The digital assistant service 118 can be configured to serve as an artificial intelligence-driven (AI-driven) conversational-type interface for the platform 114 that can conduct conversations with end users (e.g., those using the client devices 110) and perform functions and/or tasks based on the information conveyed by and/or ascertained from those conversations and other sources. The digital assistant service 118 can be configured with and/or configured to access natural language understanding (NLU) capabilities such as natural language processing, named entity recognition, intent classification, and so on. In some implementations, the digital assistant service 118 can be skill-driven in which the digital assistant service 118 includes bots that each include one or more skills for conducting conversations and performing functions and/or tasks. In some implementations, the digital assistant service 118 can be LLM-based and agent-driven in which agent(s) coordinate with LLM(s) for conducting conversations and performing functions and/or tasks. Examples of skill-driven and LLM-based and agent-driven digital assistants are described in U.S. Patent Application No. 17,648,376, filed on Jan. 19, 2022, and U.S. patent application Ser. No. 18/624,472, filed on Apr. 2, 2024, each of which are incorporated by reference as if fully set forth herein.

The digital assistant service 118 can be configured to initiate a dialog, drive a previously initiated dialog (e.g., by responding to a turn in the dialog), and/or otherwise participate in a conversation. In some implementations, the digital assistant service 118 can drive and/or participate in a dialog and/or conversation in response to events that have occurred at the client devices 110, the platform 114, the databases 122, the LLMs 124, and/or at the cloud infrastructure supporting the platform 114. In the case of a skill-driven digital assistant service 118, the events can be mapped to a particular skill and can trigger a flow for that skill. The flow can then generate response events/messages that can be used to render a user interface such as a user interface of a client application executing on the client devices 110. In the case of an LLM-based and agent-drive digital assistant service 118, the events can be mapped to a particular prompt or prompts to retrieve a result or results for the prompt or prompts, which can then be used to render the user interface. In some implementations, the digital assistant service 118 can drive and/or participate in a dialog and/or conversation in response to messages received from the client devices 110, the platform 114, the databases 122, the LLMs 1124, and/or at the cloud infrastructure supporting the platform 114. In the case of a skill-driven digital assistant service 118, the messages can be routed to a particular skill, which, as described above, can generate response events/messages for rendering the user interface. In the case of an LLM-based and agent-driven digital assistant service 118, the metadata included in the messages can be used to generate and/or access a particular prompt or prompts to retrieve a result and/or results that can be used to render the user interface.

The name entity recognition (NER) service 120 can be configured to extract named entities in interest from natural language text. NER may be used in applications that are tasked with understanding the meaning of language text. In some embodiments, the NER service 120 may be part of the digital assistant service 118. For example, NER is commonly used in natural language processing applications to identify entities in natural language text. An entity could be a word or a string of words. Given a text input, which could be one or more words, one or more sentences, one or more paragraphs, etc., NER techniques are used to identify one or more entities from the input text and associate an entity type (may also referred to as category) with each entity. For example, an entity "John Doe" may be extracted from a piece of text and tagged or labeled with a "Person" category, entity "New York" may be tagged or labeled with a "Location" category, and the like.

Some entities may be hierarchical (referred to as hierarchical entities or nested entities). For a hierarchical entity, multiple sub-entities may be associated with an extracted named entity where the tagged entity types (or categories) are hierarchically related to each other. A named entity is thus labeled at multiple levels, each level adding further details about the entity to the previous level label. For example, in the sentence "order Tylenol oral tablets," the named entity "Tylenol, tablets" may be tagged with a "medication" category (i.e., entity type) at a first hierarchical level (called level 1), and "tablets" may additionally be tagged with a "dose form" category at second hierarchical level (called level 2), where hierarchical level 2 is a sub-category (i.e., sub-entity type) of the hierarchical level 1 category (e.g., medication is a category at hierarchical level 1, and dose form is a sub-category of medication).

In certain embodiments, entities may also be categorized from a service perspective into several service categories/types, such as (1) built-in entities, (2) custom entities, (3) value list entities. The NER service 120 may include one or more machine learning models trained to label name entities with these types. Built-in entities are generic entities that can be used with a wide variety of bots. Examples of built-in entities include, without limitation, entities related to time, date, locations, addresses, numbers, email addresses, duration, recurring time periods, currencies, phone numbers, URLs, and the like.

Custom entities are used for more customized applications and may be handled by skill bots. For example, for a banking skill, an AccountType entity (part of the custom entities) may be defined by a banking skill bot designer that enables various banking transactions by checking the user input for keywords like checking, savings, and credit cards, etc. In some embodiments, a composite bag that identifies a group of related entities may be created for a particular business domain. For example, a composite bag for a pizza might include entities for type, size, crust, and extra toppings. If a user enters "I'd like a large pepperoni pizza with a gluten-free crust", the skill could extract "large", "pepperoni", and "gluten-free" from that input and not need to prompt the user for those values individually. In some applications, a composite bag may help a skill bot to prompt for individual entity values when they are missing from the user input.

Value list entities are entities based on a list of predetermined values, like menu items that are output by a common response component. A customer can optimize the entity's ability to extract user input by defining synonyms. These can include abbreviations, slang terms, and common misspellings, etc. Synonym values are not case-sensitive. For example, "USA", "United States", and "America" may be part of a value list. A technique called elastic search can utilize the value list entities to perform a faster and efficient search on a gazetteer (i.e., a list of terms or words that are named entities) to recognize specific entities or terms in a domain the skill bot operates in to improve the accuracy of entity extraction in user inputs.

The intent classification/detection service 121 can be configured to map a user's utterance to a specific task/action or category of task/action that a chatbot can perform. The intent classification service may include an intent classifier that can be trained, using machine learning, LLM-based and/or rules-based training techniques, to determine a likelihood that an utterance is representative of a task that a particular skill bot is configured to perform. In some embodiments, the intent classifier may be trained on different classes, one class for each skill bot. For example, the utterance "I need to change my flight reservation" may be categorized under the intent "change reservation" class for airline.

Although not shown, the platform 114 can include other capabilities and services such as authentication services, management services, task management services, notification services, and the like. The various capabilities and services of the platform 114 can be implemented utilizing one or more computing resources and/or servers of the platform 114 and provided by the platform 114 by way of subscriptions. Additionally, or alternatively, while FIG. 1 shows the services of the platform 114 as being separate services, one or more of the services can be combined with other services and/or be considered to be a sub-service of another service. For example, the NER service 120 and/or the intent classification/detection 121 can be a sub-service or a service that is part of the digital assistant service 118.

Medical Entity Detection and Resolution Pipeline

Figures 2A, 2B:
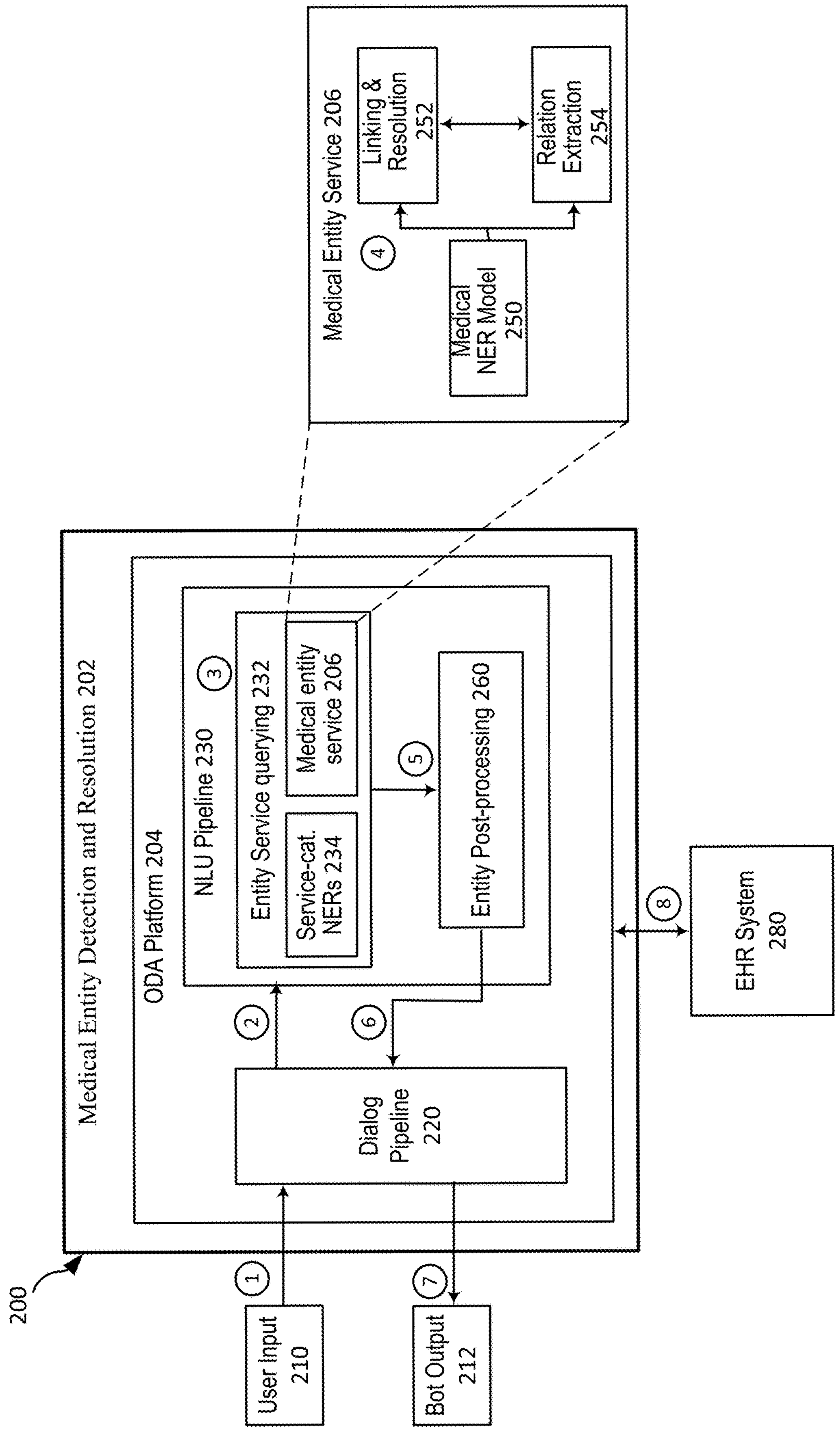
FIG. 2A is a simplified block diagram illustrating an example architecture 200 of medical entity detection and resolution pipeline, according to some embodiments.
FIG. 2B is a simplified block diagram illustrating a module of the example architecture 200 in FIG. 2A, according to some embodiments.

FIG. 2A is a simplified block diagram illustrating an example architecture 200 of medical entity detection and resolution pipeline, according to some embodiments. FIG. 2B is a simplified block diagram illustrating a module (medical entity service) of the example architecture 200 in FIG. 2A, according to some embodiments. FIGS. 2A and 2B together also illustrate the data flow and steps (shown in circled numbers) in the example architecture 200. The example architecture 200 depicted in FIG. 2 is merely an example and is not intended to unduly limit the scope of claimed embodiments. Many variations, alternatives, and modifications are possible. For example, in some implementations, the example architecture 200 may have more or fewer systems or components than those shown in FIG. 2, may combine two or more systems, or may have a different configuration or arrangement of systems. The systems, subsystems, and other components depicted in FIG. 2 may be implemented in software (e.g., code, instructions, program) executed by one or more processing units (e.g., processors, cores) of the respective systems, using hardware, or combinations thereof. The software may be stored on a non-transitory storage medium (e.g., on a memory device).

In FIG. 2A, architecture 200 can receive user input 210 (e.g., healthcare providers), perform intent detection, and medical entity detection and resolution to generate standard-compliance data structure for EHR system 280. In some embodiments, the ODA platform 204 may include a dialog pipeline 220 and NLU pipeline 230. Although shown as two pipelines, dialog pipeline 220 and NLU pipeline 230 may work together with less clear boundaries or be integrated together.

At step 1 of FIG. 2, a user (e.g., a healthcare provider) may initiate a query to the medical entity detection and resolution pipeline 202. The dialog pipeline 220 may be responsible for communicating with the user (e.g., using speech service 116 and digital assistant service 118 of FIG. 1), detecting the user's intention (e.g., using intent classification service 121 of FIG. 1) for query, and also utilize stored patient information such as patient's names and other personal information to help communicate with the user without the need to request every piece of information. For example, when a doctor asks, "When was Mary Alice's recent visit to my clinic?" The dialog pipeline 220 may provide the patient's age and residence in addition to the date of visit if this information has been stored in the dialog pipeline 220 because such information is usually requested together.

The intent detection, as discussed above in relation to intent classification/detection service 121, may be customized by the users with training data in the medical domain to specifically recognize the user's intention for query related to medical-related information, such as checking patient's health condition, lab report, etc.

At step 2 of FIG. 2, once the dialog pipeline 220 determines the user's intent is related to medical-related information, the utterance or query may be passed to NLU pipeline 230. In some embodiments, the utterance may be in the form of a text transcript or other forms that can facilitate the NER process.

At step 3 of FIG. 2, the NLU pipeline 230 may perform natural language understanding service. The NLU pipeline 230 may include an entity service query 232 and entity post-processing 260. The entity service query 232 may further include a service-category NERs module 234 and a medical entity services 206. In some embodiments, entity service query 232 may be responsible for named entity recognition (NER) as discussed above in relation to NER service 120 (discussed above), as well as services specific to medical entities. The entity post-processing 260, as its name suggested, post-process the information about the extracted named entities from the entity service query 232, such as assigning priorities to extracted named entities and normalizing data received from medical entities service 206 (discussed below).

After dialog pipeline 220 determines the user's intent is a query for medical-related information, entity service query 232 may extract entities in a received text transcript (e.g., utterances) from dialog pipeline 220 into four service categories (or four entity types): built-in entities, custom entities, value list entities, and medical entities. The first three service categories (discussed above in relation to FIG. 1) may be extracted by the service-category NERs module 234, and the fourth service category (i.e., medical entities) may be extracted by medical NER model 250 (discussed below).

In some embodiments, the service-category NERs module 234 may include three NERs responsible for detecting three different entity types based on the three service categories: built-in entities, custom entities, and value list entities, respectively. For example, a first NER in the service-category NERs module 234 may extract built-in entities. A second NER in the service-category NERs module 234 may extract custom entities. A third NER in the service-category NERs module 234 may extract value list entities. These NERs in the service-category NERs module 250 may perform named entity recognition in parallel.

The medical entity services 206 (shown in FIG. 2B) may include a medical NER model 250 specialized in detecting medical entities. This medical NER model 250 may also perform named entity recognition in parallel with the NERs in the service-category NERs module 234. Medical entities are a group of entities belonging to medical entity types, such as diagnosis, immunization, lab_test, allergent agent, vitals, etc., for digital assistance in the medical field.

For the purpose of this disclosure, the extracted named entities may also be referred to as tokens. A token may be a single unit of text, which can be a word, a subword, a punctuation mark, a number, or a symbol. Named entities (or tokens) may be extracted from utterance by the NLU pipeline, and then labeled with different entity types (e.g., service categories).

Some entities in these four service categories may overlap. For example, custom entities for a particular skill under the medical domain may overlap with the medical entities. As an example, a query from a healthcare provider may be "When was Mary Alice's recent visit to my clinic?" and "What was her blood pressure?" The named entities, "Mary Alice, visit, and my clinic," may fall into the categories of built-in entities and/or value list entities, and are non-medical entities. On the other hand, the named entity "blood pressure" may fall into the categories of custom entities and medical entities.

In FIG. 2B, the medical entity service 206 may include the medical NER model 250 as discussed above, linking and resolution module 252, and relation extraction module 254. In some embodiments, medical NER model 250 may detect and extract medical entities from the utterance, and label the extracted medical entities with various medical entity types, The linking and resolution module 252 may identify an appropriate medical coding system supporting each labeled medical entity type, link the extracted medical entities to corresponding medical codes in the identified medical coding system, and construct a Fast Healthcare Interoperability Resources (FHIR)-compliance data structure. FHIR is a standard for exchanging healthcare information electronically.

The medical NER model 250 may recognize and extract the received entities as medical entities and associate each medical entity with a particular medical entity type. Because no one medical coding system can support all types of medical entities, a trained medical NER model 250 can help identify (recognize or extract) medical entities from the utterance, and label these medical entities with proper medical entity types to enable the association between the extracted medical entities with medical coding systems. This association is performed by the linking and resolution module 252 (discussed below).

In some embodiments, the medical NER model 250 (an example of the first machine learning model) may be a machine learning (ML) model trained by supervised learning techniques in the medical domain. The training data may include training natural language utterances, where each training natural language utterance (e.g., "What was John's cholesterol level?") is labeled with medical entities (e.g., cholesterol level) and their associated medical entity types (e.g., lab test). Therefore, the medical NER model 250 can be trained to recognize medical entities from natural language utterances and also their respective medical entity types. The medical entity types may also be referred to as class labels, and each type may be referred to as a class.

The medical entity types may include at least twenty-seven types (e.g., allergent agent, diagnosis, lab test, medication, immunization, vitals, etc.) under the Fast Healthcare Interoperability Resources (FHIR) standard. Some medical entity types may be hierarchical entity types (or nested entity types), such as medication entity type. For example, utterances (or queries) from a healthcare provider may include the following sentences:

"When was Mary Alice's visit to my clinic?"

"What was her blood pressure?"

"Please order Tylenol 200 milligram oral tablets."

In the above sentences, the tokens, "blood pressure", Tylenol", and "tablets" may be extracted as medical entities and labeled by medical NER model 250 with their corresponding medical entity types. For example, entity (or token) "blood pressure" may be labeled with "vitals" entity type. Entities "Tylenol" and "tablet" are both labeled with "medication" entity type. However, because medication entity type is a hierarchical entity type, the entity "Tylenol" may be further labeled or associated with "ingredient" sub-type, while the entity "tablets" may be further labeled or associated with "dose form" sub-type.

At step 4 of FIG. 2, the labeled medical entities and their associated medical entity types may be provided to linking and resolution module 252 and relation extraction module 254. The linking and resolution module 252, in some embodiments, may be responsible for linking a medical code of a medical coding system to a medical entity and constructing a FHIR-compliance data structure. Additionally, a relation extraction module 254 may help identify and extract quantity related to one or more medical entities in the utterances. For example, the utterance ("John's cholesterol level is 180 mg/dL.") contains a quantity "230" that is associated with the medical entity "cholesterol level." The relation extraction module 254 can recognize that relation, and extract the quantity "180" accordingly. In some embodiments, linking and resolution module 252 and relation extraction module 254 may be integrated together.

As discussed above, there are many public medical coding systems (also referred to as standardized ontologies) created based on the FHIR standard, where each coding system may cover one or more medical entity types. For example, Systematized Nomenclature of Medicine—Clinical Terms (SNOMED CT) may cover general health problems and condition disease. Prescription Normalization (RxNORM) is specialized in medication. Logical Observation Identifiers Names and Codes (LOINC) may cover observation, such as lab test. International Classification of Diseases, 10th Revision (ICD-10) may cover diagnosis. Within each coding system, there are codes for entities belonging to the medical entity type that the coding system supports. For example, in SNOMED CT coding system covering medical entity type "vitals," a particular code "13579" may be used to represent an entity "blood pressure."

During the linking process, the linking and resolution module 252 may identify an appropriate medical coding system for the labeled medical entity type in the utterance and then find codes representing the medical entities (or tokens or the extracted named entities) associated with that medical entity type. For example, continuing with the above example regarding the query "Please order Tylenol 200 milligram oral tablets", the medical entity "tablets" belongs to the "medication" entity type, and thus, the RxNorm coding system may be identified. In some embodiments, such a linking process of identifying the appropriate medical coding system may use a mapping table, key-value pair database, and the like.

Furthermore, once the medical coding system is identified, a code (e.g., 67890) within the RxNorm coding system representing medical entity "tablets" may also be retrieved. In some embodiments, finding a code in a coding system may utilize a technique called cosine similarity search. The synonyms of names associated with the codes in a coding system may be embedded into vectors, which are stored in a vector database. When a medical entity needs to be mapped to a code in a particular coding system, that medical entity can be embedded into a vector. Then, a cosine similarity search may be performed against all codes in that particular coding system based on that vector to find the best match. For example, for RxNorm coding system, "Tylenol 200 mg" associated with a code "12345" may be embedded into a first vector. "Tylenol" only (representing a general Tylenol) associated with another code "23456" may be embedded into a second vector. The first and second vectors may both be stored in the vector database. When the extracted medical entity (e.g., "Tylenol 200 mg oral tablets") needs to be mapped to an RxNorm code, it is embedded into a third vector, which may be used to perform cosine similarity search in the vector database to find the best match, which is the first vector with code "12345." Those skilled in the art will appreciate various ways and techniques that can be used to measure vector similarity to find the medical codes. The techniques may include, but not limited to, Euclidean Distance, Inner product, and the like.

In some embodiments, two or more medical coding systems may have some overlaps, such as covering the same medical entity type. For example, both SNOMED CT and ICD-10 may cover some medical entities under entity type "diagnosis." In such case, linking and resolution module 252 may reference all codes in each medical coding system and select the coding system that is most related to the detected medical entities.

During the resolution process, the linking and resolution module 252 may construct a FHIR-compliance data structure using the identified medical coding system, and the codes. Such data structure may be a structured framework for recording and exchanging healthcare information electronically. In some embodiments, a format, such as JavaScript Object Notation (JSON) may be used.

In some embodiments, the linking and resolution module 252 may be a machine learning (ML) model (e.g., bidirectional encoder representations from Transformers (BERT)) that is trained using unsupervised learning techniques. The training data may include data structures (e.g., FHIR-compliance data structure) including medical codes associated with medical entities (e.g., cholesterol level), medical entity types (e.g., lab test) associated with the medical entities, and medical code systems (e.g., LOINC) associated with the medical entity types.

Figure 3A:
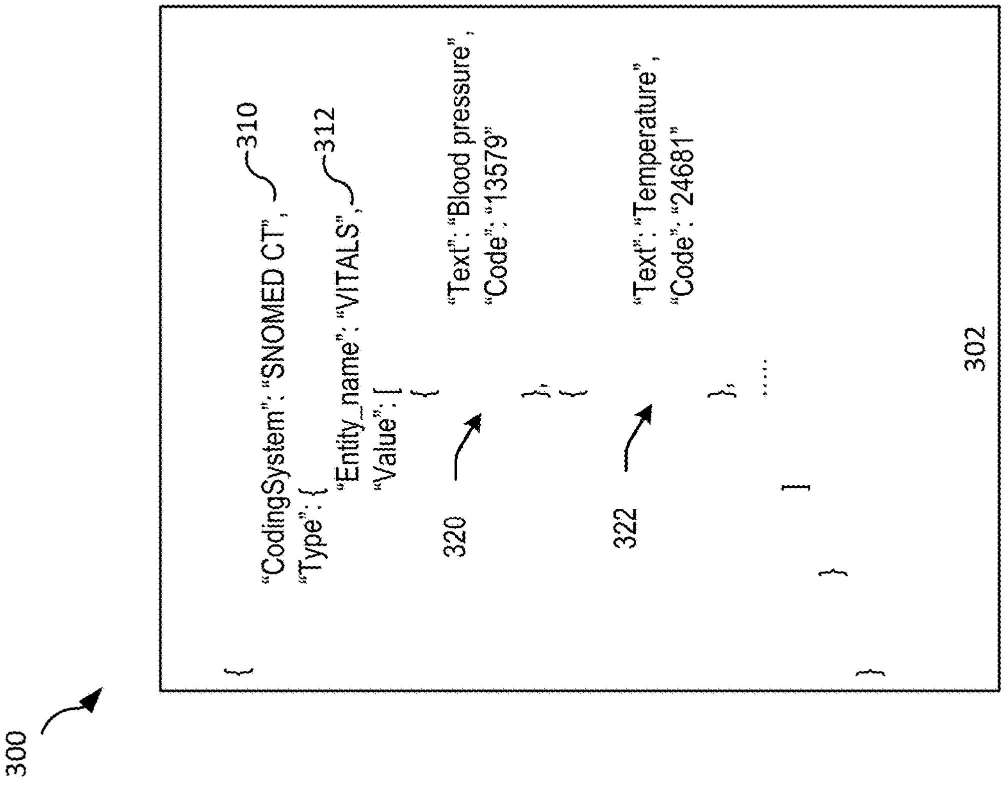
FIG. 3A is an example of data structure generated by a medical entity detection and resolution pipeline, according to some embodiments.
Figure 3B:
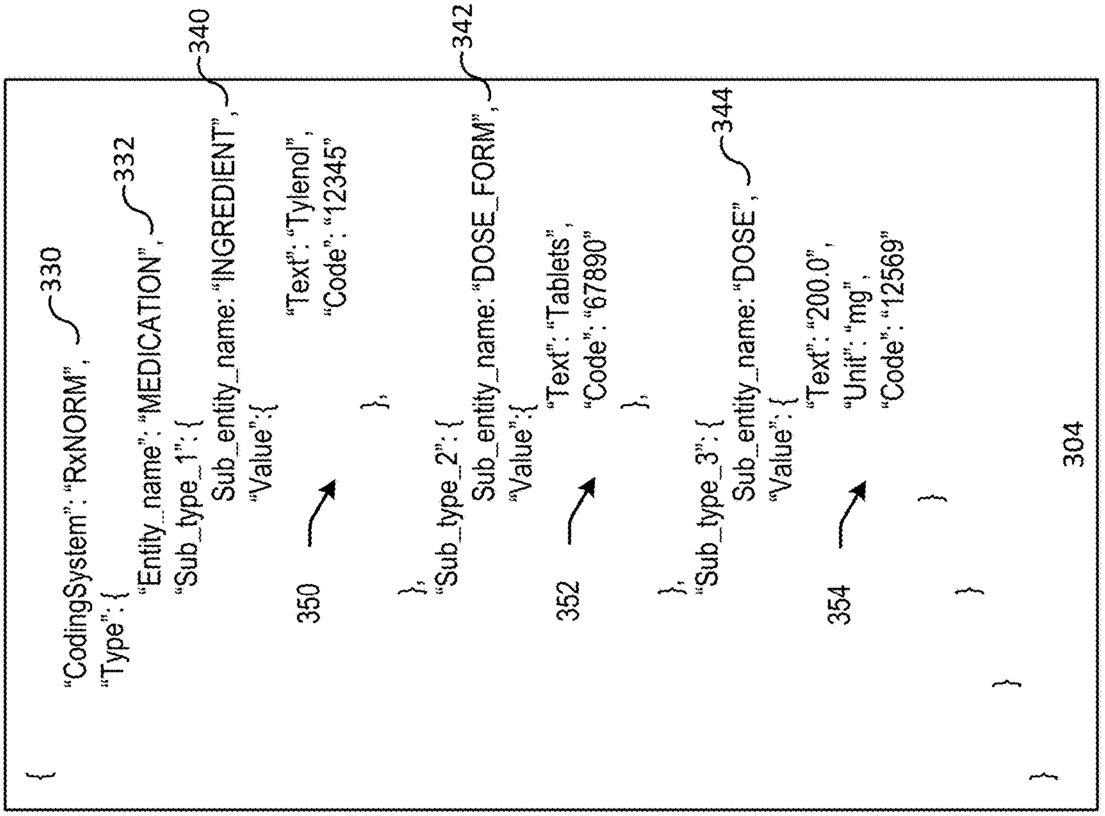
FIG. 3B is an example of data structure generated by a medical entity detection and resolution pipeline, according to some embodiments.

Turning to FIGS. 3A and 3B. These two figures illustrate data structures generated by a medical entity detection and resolution pipeline, according to some embodiments. As discussed above, a FHIR-compliance data structure may be generated based on the labeled medical entity types after collecting the data involving medical coding systems and the codes associated with the extracted medical entities.

FIG. 3A illustrates a FHIR-compliance data structure (or schema) 302 generated based on medical entity type "vitals." For example, a query (or utterance) by a healthcare provider may be the following:

"What were Mary Alice's vitals?"

This utterance may be processed by the NLU pipeline 230, which includes service-category NERs 234 and medical NER model 250 of the medical entity service 206, to extract the entity "vitals," and interpreted to include commonly known medical entities, "blood pressure," "heart rate," "temperature," etc. under the umbrella term "vitals" (or vital signs) based on the combination of service categories, such as custom entities, value list entities, and medical entities. The medical NER model 250 may further label this group of medical entities with the same medical entity type "vitals." The linking and resolution module 252 may then identify SNOMED CT coding system to associate with the medical entity type "vitals," and find corresponding codes for this group of medical entities. A FHIR-compliance data structure 302 in JSON format may then be generated, as shown in FIG. 3A.

In FIG. 3A, the field coding system 310 contains "SNOMED CT" that covers the medical entity type "vitals" in field type/entity_name 312. Under the "vital" entity type, there are two medical entities associated with their corresponding codes. For example, value block 320 includes medical entity "blood pressure" and its associated code "13579." Value block 322 includes medical entity "temperature" (in text field) and its associated code "24681" (in code field).

FIG. 3B illustrates a FHIR-compliance data structure (or schema) 304 generated based on medical entity type "medication." As discussed above, "medication" may be a hierarchical entity type (or nested entity type), which may include at least seven sub-entity types (also referred to as seven medication attributes), such as ingredient, as needed, route, dose form, frequency, dispense, and refill. In some embodiments, two additional sub-entity types, dose and strength may be included. For example, a query (or utterance) by a healthcare provider may be the following:

"Please order Tylenol 200 milligram oral tablets."

The medical NER model 250 may label "Tylenol" and "tablet" are both labeled with "medication" entity type, and additionally with "ingredient" sub-type for "Tylenol," and "dose form" sub-type for "tablets." The linking and resolution module 252 may then identify RxNORM coding system to associate with the medical entity type "medication," and corresponding codes for these medical entities. Furthermore, the relation extraction module 254 may extract the quantity "200" related to medical entities "Tylenol" and "tablets."

As shown in FIG. 3B, the field, coding system 330, contains "RxNORM" that covers the medical entity type "MEDICATION" in the field, type/entity_name 332, at a first hierarchical level. Inside the type/entity_name field 332, three additional sub-fields (340, 342, and 344) are listed to associate with the medical sub-entity types at the second hierarchical level. Each sub-field has a value block that includes the medical entity and its associated code. For example, at the second hierarchical level, the sub-field, sub_type_1/sub_entity_name 340, includes "INGREDIENT," and value block 350 that includes medical entity "Tylenol" (in the text field) and its associated code "12345." The sub-field, sub_type_2/sub_entity_name 342, includes "DOSE_FORM," and value block 352 that includes medical entity "Tablets" (in the text field) and its associated code "67890." The sub-field, sub_type_3/sub_entity_name 344, includes "DOSE," and value block 354 that includes medical entity "200.0" (in the text field) with unit as "mg," and its associated code "12569."

In some embodiments, data structures 302 and 304 in FIGS. 3A and 3B generated by the medical entity service 206 may be in the same format (e.g., JSON). In other embodiments, a data structure, such as the one in FIG. 3A, may include two or more medical entity types, and each medical entity type may be a section (equivalent to field type/entity_name 312) within the data structure.

Referring back to FIG. 2, at step 5, the generated FHIR-compliance data structures incorporating medical-related information and other information, such as non-medical entities, may be provided to entity post-processing module 260.

As discussed above, in some embodiments, the entity post-processing 260 module may perform aggregation by assigning priorities to extracted named entities, and also normalizing data received from entity service querying 232. In some embodiments, higher priority may be assigned to medical entities that have been labeled with medical entity types, while lower priority may be assigned to non-medical entities. In other embodiments, priorities may be assigned to entities based on service categories (e.g., built-in entities, custom entities, value list entities/elastic search, and medical entities), and aggregate the result. For example, high priorities may be assigned to entities extracted under the built-in entity category and medical entity category. The entities extracted under the value list entities/elastic search category and custom entity category may be evaluated. If the entities under these two categories overlap with medical entities, these overlap medical entities are assigned with high priority. In some embodiments, two or more levels of priorities (e.g., high, and low priorities) may be used. In other embodiments, other ways of assigning priorities may be contemplated, such as using numerical prioritization, depending on the applications.

The entity post-processing 260 module may also normalize data to certain formats that are compatible with the EHR system 280. For example, a non-medical entity (e.g., 100 dollars) extracted under the built-in entity category may be normalized to "100.00 USD." As another example, the quantity "200 milligrams" for Tylenol tablets may be normalized to "200.0 mg."

At step 6 of FIG. 2, the entity post-processing 260 may inform the dialog pipeline 220 of the completion of the medical entity detection and resolution process, and such that, at step 7, the dialog pipeline 220 can generate a response to the natural language utterance from the user based on the generation of one or more data structures, such as providing user-friendly confirmation and feedback to complete the user interaction loop. At step 8, the medical-related information requested by the user (e.g., healthcare provider), including the FHIR-compliance data structures, incorporating the extracted and labeled entities under different service categories may be stored in the database 122 of an EHR system 124. Because the patient records stored in the EHR system 124 are in standardized codes, the medical information in patient records can be retrieved efficiently using standard medical codes based on the user's utterance through the medical entity detection and resolution pipeline 202.

Figure 4:
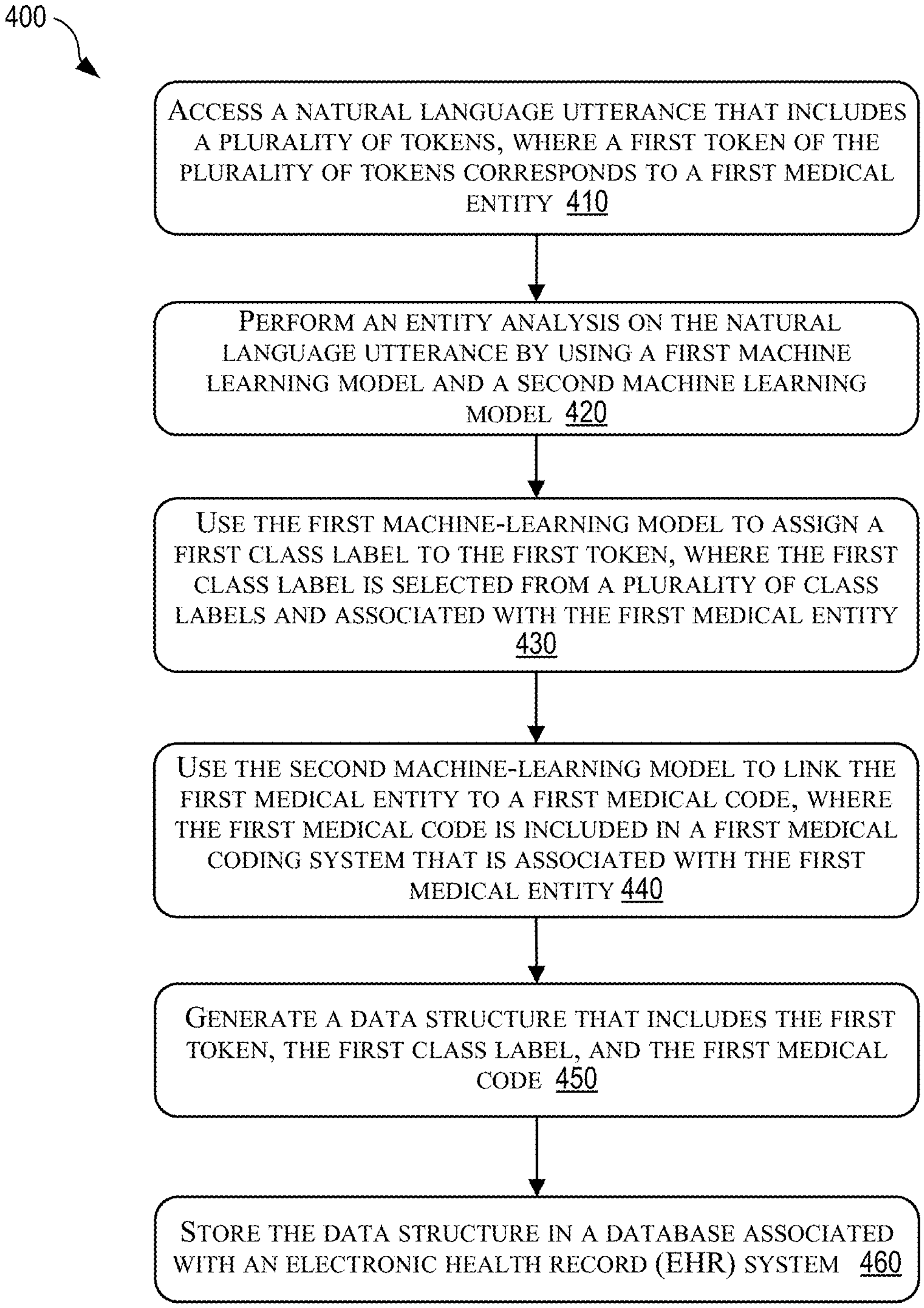
FIG. 4 is a flowchart illustrating processing performed by a medical entity detection and resolution pipeline, according to certain embodiments.

FIG. 4 is a flowchart illustrating processing performed by a medical entity detection and resolution pipeline, according to certain embodiments. The processing depicted in FIG. 4 may be implemented in software (e.g., code, instructions, program) executed by one or more processing units (e.g., processors, cores) of the respective systems, using hardware, or combinations thereof. The software may be stored on a non-transitory storage medium (e.g., on a memory device). The method presented in FIG. 4 and described below is intended to be illustrative and non-limiting. Although FIG. 4 depicts the various processing steps occurring in a particular sequence or order, this is not intended to be limiting. In certain alternative embodiments, the processing may be performed in some different order or some steps may also be performed in parallel. It should be appreciated that in alternative embodiments the processing depicted in FIG. 4 may include a greater number or a lesser number of steps than those depicted in FIG. 4.

At step 410, a natural language utterance that includes a plurality of tokens may be accessed, and a first token of the plurality of tokens corresponds to a first medical entity. For example, in FIGS. 2A & 2B (referred to as FIG. 2), the dialog pipeline 220 may access the natural language utterance (e.g., "what is Mary Alice's temperature?") from a user 210 (e.g., a doctor). A first token (e.g., "temperature") in the utterance may be a medical entity.

At step 420, an entity analysis may be performed on the natural language utterance by using a first machine learning model and a second machine learning model. For example, in FIG. 2, two machine learning models, medical NER model 250 and linking and resolution module 252, as part of the NLU pipeline 230, may be used to perform entity analysis. The entity analysis may include performing named entity recognition on the natural language utterance as well as linking the recognized/extracted named entities that are medical entities to standardized codes for storing in an EHR system database.

At step 430, the first machine-learning model may be used to assign a first class label to the first token, where the first class label is selected from a plurality of class labels and associated with the first medical entity. For example, in FIG. 2 and FIGS. 3A & 3B (referred to as FIG. 3), the medical NER model 250 may detect and extract the word "temperature" in the above example as a medical entity, and assign a class label, which may be a medical entity type (e.g., vitals 312 of FIG. 3A) to the word "temperature." The medical entity type may be one of the at least twenty-seven medical entity types (or class labels), such as allergent agent, diagnosis, lab test, medication, immunization, vitals, etc.

At step 440, the second machine-learning model may be used to link the first medical entity to a first medical code, where the first medical code is included in a first medical coding system that is associated with the first medical entity. For example, in FIG. 2 and FIG. 3, the linking and resolution module 252 may link the extracted medical entity ("temperature") to a medical code (e.g., "24681" of block 322 of FIG. 3A) in the SNOMED CT coding system 310 because this coding system is associated with (or specialized in) medical entity type "vitals" to which the medical entity "temperature" belongs. As discussed in step 4 of FIG. 2B, the medical entity type "vitals" may be mapped to an appropriate medical coding system of many public medical coding systems (SNOMED CT, RxNORM, LOINC, and ICD-10). Then, a cosine similarity search technique may be used to find a code (e.g., "24681") in the mapped coding system (e.g., SNOMED CT) that best matches the medical entity (e.g., "temperature").

At step 450, a data structure that includes the first token, the first class label, and the first medical code is generated. For example, in FIG. 2 and FIG. 3, the FHIR-compliance data structure 302 may be created by the linking and resolution module 252. The data structure 302 may be in JSON format and include the medical entity "temperature" and medical code "24681", as shown in block 322, and the medical entity type "vitals" 312. In some embodiments, data (e.g., quantity such as "90 Fahrenheit") related to the medical entity (e.g., "temperature") in the data structure may be normalized to a format (e.g., "90.0° F.") that conforms to a the EHR system 280.

At step 460, the data structure may be stored in a database associated with an electronic health record (EHR) system. For example, in FIG. 2, the FHIR-compliance data structure 302 generated by the linking and resolution module 252 of medical entity service 206 may be stored in the EHR system 280.

Medication Order Pipeline

Figure 5:
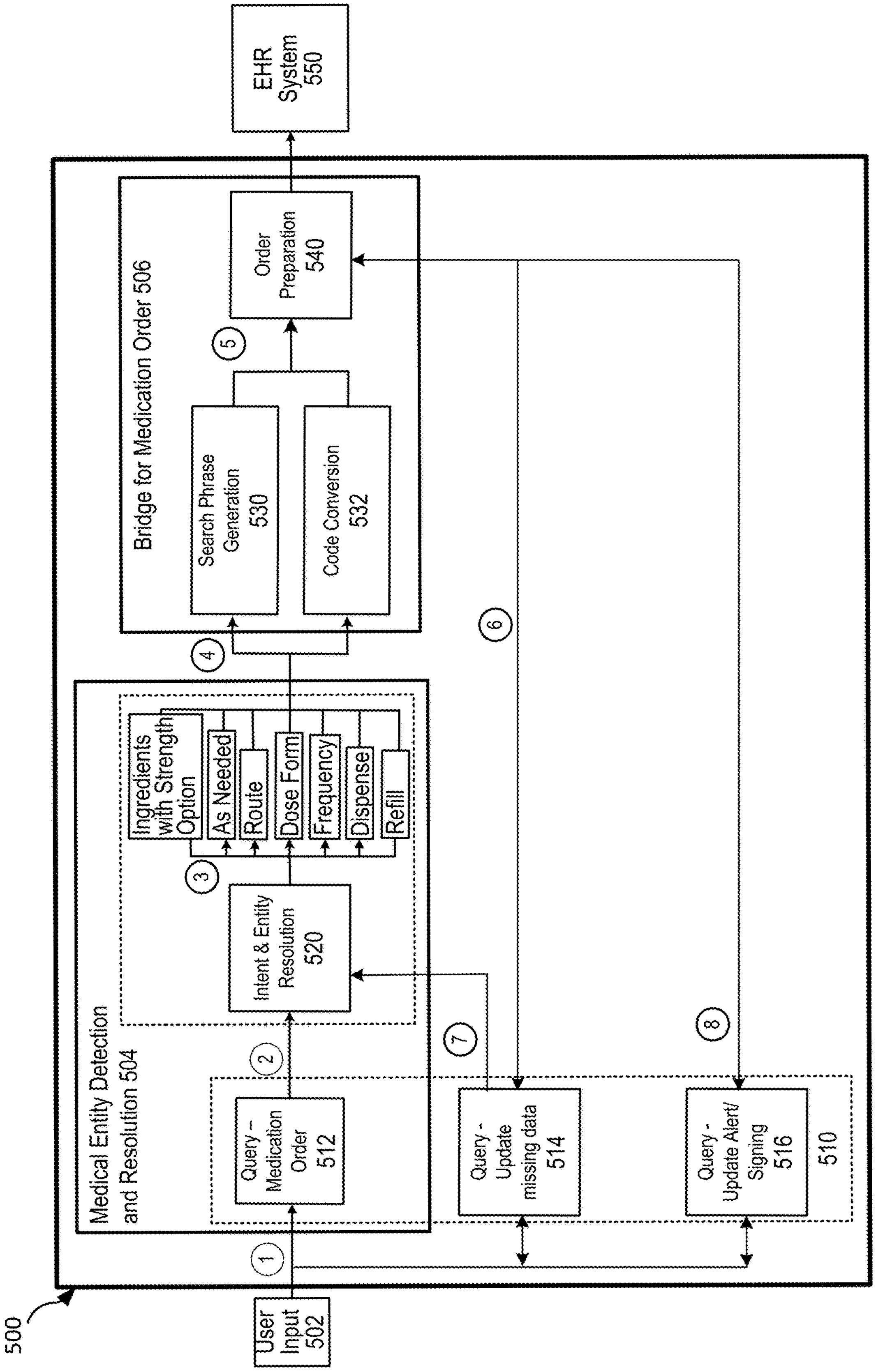
FIG. 5 is a simplified block diagram illustrating an example architecture 600 of medication order pipeline, according to some embodiments.

FIG. 5 is a simplified block diagram illustrating an example architecture 500 of the medication order pipeline, according to some embodiments. FIG. 5 also illustrates the data flow and steps (shown in circled numbers) in the example architecture 500. In FIG. 5, the example architecture 500 may include a medical entity detection and resolution pipeline 504, a bridge for medication order pipeline 506, query—updating missing data module 512, and query—update alert/signing module 514.

At step 1 of FIG. 5, medical entity detection and resolution pipeline 504 may receive user input 502 (e.g., utterances or queries). The medical entity detection and resolution pipeline 504 may be similar to the medical entity detection and resolution pipeline 202 described in FIG. 2. However, medical entity detection and resolution pipeline 504 may focus on detecting medical entities associated with the medication entity type. The medical entity detection and resolution pipeline 504 further includes a query—mediation ordering module 510, and an intent and entity resolution pipeline 520. An additional query stage 510 includes a query—mediation ordering module 512, a query—updating missing data module 514, and a query—updating alert/signing module 516. The query stage 510 may be separately shown for the purpose of illustrating interaction with the user at different steps of the medication order pipeline 500.

The query—mediation ordering module 510 may be similar to the communication portion of dialog pipeline 220 of FIG. 2 that utilizes speech service 116 and digital assistant service 118 of FIG. 1. The query—mediation ordering module 510 can perform conversation with the user to receive a query about mediation order.

At step 2 of FIG. 5, the intent and entity resolution pipeline 520 may be similar to the ODA platform 204 and medical entity service 206 of FIG. 2. The intent and entity resolution pipeline 520 may perform intent classification/detection, named entity recognition, link medical entities to corresponding codes of various coding systems, and generate a data structure. For this medication order pipeline 500, the intent and entity resolution pipeline 520 may detect an intent for a medication order first before the other processes can be performed. If the detected intent is not for medication orders, such as a query for patient information, the process may stop at step 2.

At step 3 of FIG. 5, once an intent for a medication order is detected, intent and entity resolution pipeline 520 can link the medication entity type to the RxNORM coding system, find one or more codes within the RxNORM coding system using cosine similarity search to match the extracted medication entities. As discussed above in relation to FIG. 3B, the medication entity type may be a hierarchical entity type (or nested entity type), which may include at least seven sub-entity types, including ingredient, as needed, route, dose form, frequency, dispense, and refill. The medical entities (e.g., "Tylenol," "tablet," and "200 milligrams") may be mapped to different medical sub-entity types (e.g., ingredient, dose_form, and dose) and corresponding codes, as shown in FIG. 3B. A FHIR-compliance data structure 304 may also be generated based on the utterance for medication order.

At step 4, bridge for medication order pipeline 506 may receive the data structure. The medication order pipeline 506 includes two modules representing two parallel pipelines, search phrase generation pipeline 530 and code conversion pipeline 532. These two pipelines may be two options (or different APIs) for generating medication order information acceptable by the EHR system 550.

The first option may be performed by search phrase generation pipeline 530, which may include a medication order catalog API. It may use the data structure (shown in FIG. 3B) for medication entity type to construct a search phrase. In some embodiments, the search phrase may be a string that concatenates keywords for searching one or more order catalogs. For example, suppose an input utterance from the user contains a sentence that separates medical entities far apart:

"Please order Tylenol to help alleviate Mary's headache using oral tablets, and let's start with 200 milligrams."

The medical entity detection and resolution 504 may be able to perform entity analysis on the above natural language utterance, and generate the data structure 304 shown in FIG. 3B. The search phrase generation pipeline 530 can then identify the keywords (i.e., the medical entities), "Tylenol" from block 350, "tablets" from block 352, "200.0 mg" from block 354, and other blocks that contain "oral" (not shown). These keywords can be concatenated to form a concise search phrase:

"Tylenol 200 mg oral tablets"

In some embodiments, the search phrase may be generated using a rule-based method. For example, the rule for generating a search phrase may concatenate medical entities associated with different sub-entity types in the following order: ingredients, dose, route, dose form, frequency, refill, etc. In some embodiments, other methods may be used, such as the knowledge graph-based method, or even use a language model.

The second option may be performed by code conversion pipeline 532, which may include an API that can convert standard codes to another type of codes. Some EHR systems (e.g., Cerner) may have their EHR system-specific or proprietary medical codes or accept non-standard codes. For example, a non-standard medical coding system called Clinical Knowledge Identifier (CKI) may be used by certain EHR systems. CKI may be used for general medication. In CKI coding system, Tylenol 200 mg tablets and Tylenol 500 mg tablets may all be mapped to the same code rather than different codes such as the standard RxNorm coding system. In some embodiments, the medical entity detection and resolution 504 may be designed to generate CKI codes for medical entities (e.g., "Tylenol," "tablet,").

In other embodiments, for an EHR system that uses its own EHR system-specific medical codes, one RxNorm code, such as "12345" for Tylenol in block 350 of FIG. 3B, may be converted to a first EHR system-specific medical code. Another RxNorm code, such as "67890" for tablets in block 352 of FIG. 3B, may be converted to a second EHR system-specific medical code.

At step 5 of FIG. 5, the medication order information, such as a search phrase generated by search phrase generation pipeline 530 or converted medical codes generated by code conversion pipeline 532, may be provided to ordering preparation module 540. In some embodiments, the choice of using which option/route (e.g., first option or second option) may be determined by the latencies of the APIs associated with these two option pipelines. Both pipelines in bridge 506, search phrase generation pipeline 530 and code conversion pipeline 532 may be performed in parallel. If the medication order catalog API (i.e., option 1) has shorter latency (e.g., lower traffic or faster processing), the search phrase may be provided to the ordering preparation module 540. If the code-conversion API (i.e., option 2) has a shorter latency, the converted medical codes may be provided to the ordering preparation module 540.

In some embodiments, the code conversion module 532 may be a machine-learning model trained using unsupervised learning techniques. In some embodiments, if an EHR system (e.g., 280) can accept and use standard medical codes, such as RxNORM codes, such codes may be provided directly to the EHR system without conversion.

At step 6 of FIG. 5, the order preparation module 540 (e.g., an API for new medication orders) may be responsible for checking any missing data received from the bridge for medication order pipeline 506. For example, if a received search phrase ("Tylenol oral tablets") under option 1 (under search phrase generation pipeline 530) has missing data about the dose (e.g., "200 mg"), the order preparation module 540 may send a request to the query—updating missing data module 514 to communicate to user 502, and ask for more information. For option 2 (under code conversion pipeline 532), the missing data may be a medication code related to the dose. In some embodiments, a composite bag for medication may be utilized to help check the missing data. For example, a composite bag for medication may include synonyms of medical entities associated with the at least seven sub-entity types. If any of the at least seven sub-entity types is missing, the order preparation module can 540 detect such missing data.

At step 7 of FIG. 5, after the query—updating missing data module 514 receives the updated information about missing data (e.g., "200 mg"), this updated information may go through the medical entity detection and resolution pipeline 504 and bridge for medication order pipeline 506, as discussed above. For example, a new utterance from the user (e.g., healthcare provider) containing the updated information may be "Please add 200 mg to Tylenol oral tablets," which may be detected as medication ordering intent, and medical entities (e.g., Tylenol, oral, tablets, and 200 mg) may be recognized, mapped to RxNorm codes. The new search phrase or converted codes can then be processed again by the order preparation module 540.

At step 8 of FIG. 5, the order preparation module 540 may also be responsible for requesting the user to sign the medication order or providing updates to the user about the status of the medication order. For example, when order preparation module 540 has checked and confirmed all required data (or information) is available, it may request the query—update alert/signing module 516 to communicate to the user (e.g., healthcare provider, doctor) to sign the medication order to complete the order process. The signed order may be sent back to the order preparation module 540.

Additionally, when the medication order has been sent to the EHR system 550 and fulfilled (e.g., forwarded to a pharmacy), a confirmation may be communicated to user 502 through the query—update alert/signing module 516. On the other hand, if the medication order is out of stock or other issues need to be resolved, the order preparation module 540 may also request the query—update alert/signing module 516 to notify user 502.

Figure 6:
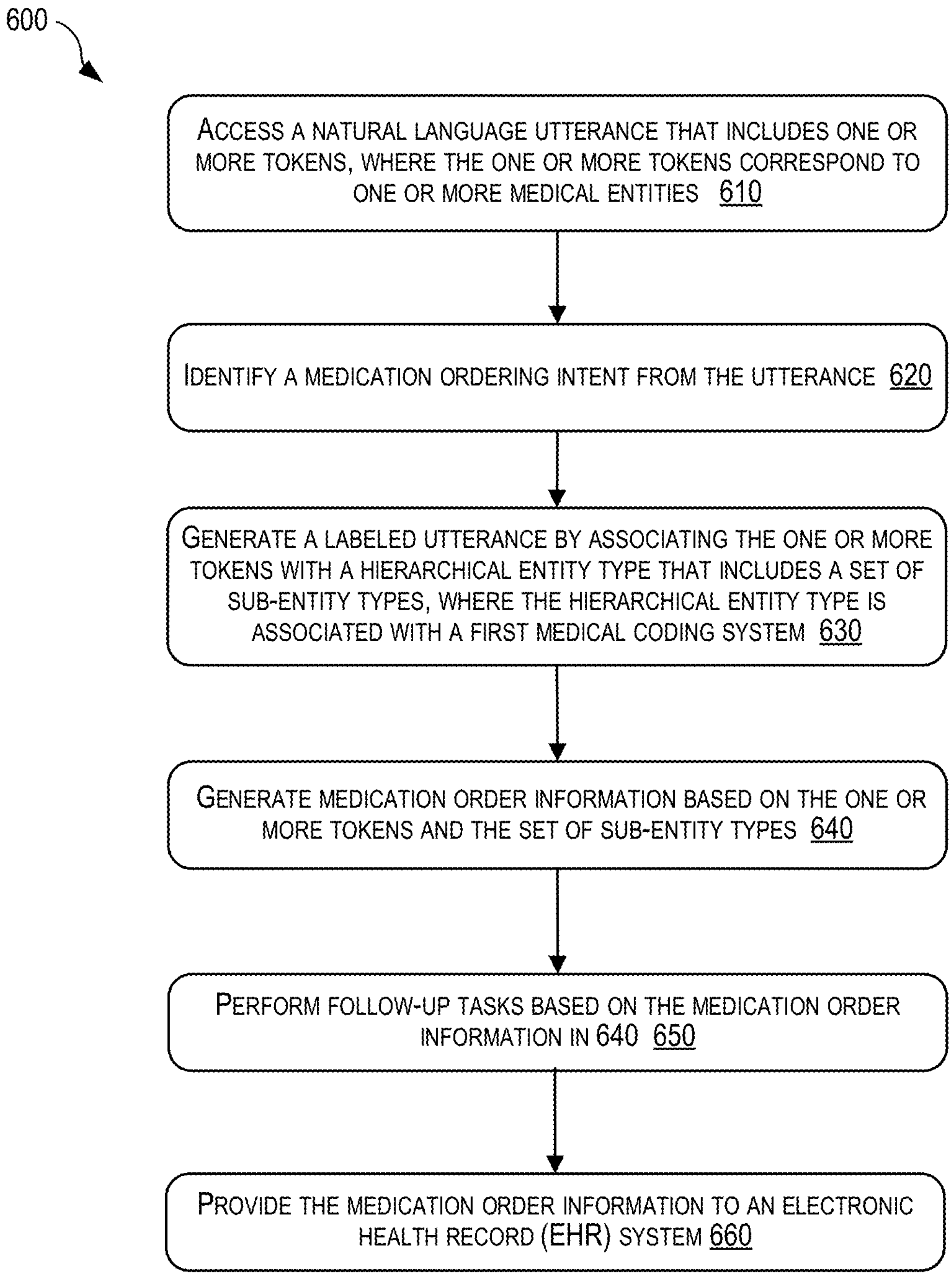
FIG. 6 is a flowchart illustrating processing performed by a medication order pipeline, according to certain embodiments.

FIG. 6 is a flowchart illustrating processing performed by a medication order pipeline, according to certain embodiments. The processing depicted in FIG. 6 may be implemented in software (e.g., code, instructions, program) executed by one or more processing units (e.g., processors, cores) of the respective systems, using hardware, or combinations thereof. The software may be stored on a non-transitory storage medium (e.g., on a memory device). The method presented in FIG. 6 and described below is intended to be illustrative and non-limiting. Although FIG. 6 depicts the various processing steps occurring in a particular sequence or order, this is not intended to be limiting. In certain alternative embodiments, the processing may be performed in some different order or some steps may also be performed in parallel. It should be appreciated that in alternative embodiments the processing depicted in FIG. 6 may include a greater number or a lesser number of steps than those depicted in FIG. 6.

At step 610, a natural language utterance that includes one or more tokens is accessed, where the one or more tokens correspond to one or more medical entities. For example, in FIG. 5, the query—medication order module 512 may access the natural language utterance (e.g., "Please order Tylenol to help alleviate headache using oral tablets, and let's start with 200 milligrams.") that includes many tokens from a user 210 (e.g., a doctor). The tokens (e.g., Tylenol, tablets, 200 milligrams) may correspond to medical entities.

At step 620, a medication ordering intent may be identified from the natural language utterance. For example, in FIG. 5, the intent and entity resolution pipeline 520 may detect and identify a medication ordering intent based on the one or more tokens (e.g., "order" and "Tylenol") in the natural language utterance.

At step 630, a labeled utterance may be generated by associating the one or more tokens with a hierarchical entity type that includes a set of sub-entity types, where the hierarchical entity type is associated with a first coding system. Continuing with the above example, in FIG. 5, the intent and entity resolution pipeline 520 may recognize and label the one or more tokens (e.g., "Tylenol," "oral," "tablet," and "200 milligrams") as medical entities and their associated medication entity type. As discussed above in relation to FIGS. 1-3, the medication entity type may include at least seven sub-entity types, such as ingredient, as needed, route, dose form, frequency, dispense, and refill, as shown in step 3 of FIG. 5. The medication entity type may be associated with RxNORM coding system (an example of the first coding system) based on the FHIR standard.

At step 640, medication order information may be generated based on the one or more tokens and the set of sub-entity types. For example, in FIG. 5, the medication order information may include a search phrase (e.g., "Tylenol 200 mg oral tablets") generated search phrase generation pipeline 530, or EHR system-specific medical codes converted from RxNORM codes for these medical entities (e.g., Tylenol, 200 mg, oral, and tablets), by code conversion pipeline 532. The "200 mg" may be a normalized value of "200 milligrams" as discussed above.

At step 650, follow-up tasks based on the medication order information in 640 may be performed. For example, in FIG. 5, the medication order information may be processed by the order preparation module 540, and some follow-up tasks may be performed before sending to an EHR system. The order preparation module 540 may work with the query—updating missing data module 514 and the query—update alert/signing module 516 to perform the follow-up tasks, which may include verifying (or checking) any missing data (e.g., missing dose "200 mg") in the medication order information, requesting a signature from the user, or providing an update alert (e.g., out-of-stock).

At step 660, the medication order information may be provided to an electronic health record (EHR) system. Once the medication order information has been verified to be completed, and the signature of the user (e.g., doctor) has been obtained, the information can be provided to the EHR system 550 to fulfill the order (e.g., forwarded to a pharmacy). A confirmation may be communicated to the user through the query—update alert/signing module 516.

Figure 7:
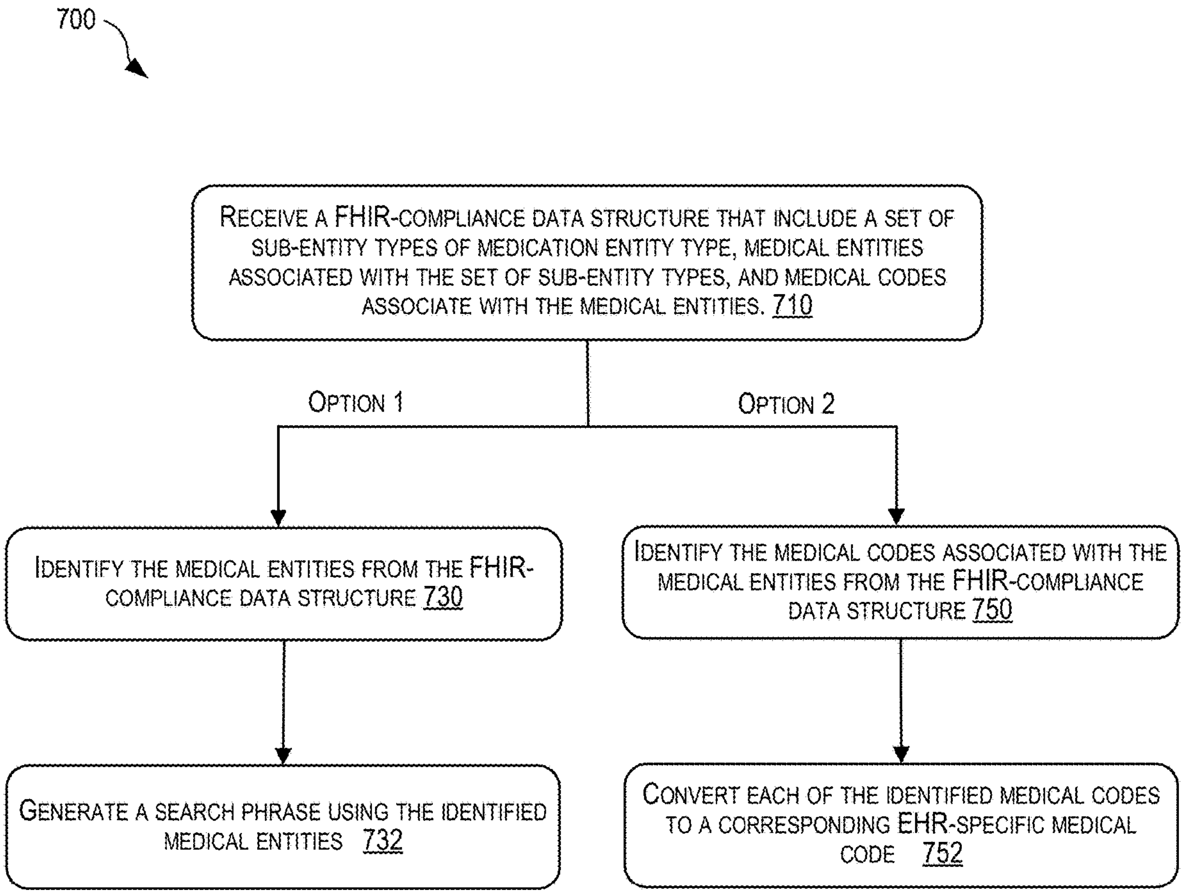
FIG. 7 is a flowchart illustrating example methods for generating medication order information, according to certain embodiments.

FIG. 7 is a flowchart illustrating example methods for generating medication order information, according to certain embodiments. FIG. 7 may provide further details on step 640 of FIG. 6. The processing depicted in FIG. 7 may be implemented in software (e.g., code, instructions, program) executed by one or more processing units (e.g., processors, cores) of the respective systems, using hardware, or combinations thereof. The software may be stored on a non-transitory storage medium (e.g., on a memory device). The method presented in FIG. 7 and described below is intended to be illustrative and non-limiting. Although FIG. 7 depicts the various processing steps occurring in a particular sequence or order, this is not intended to be limiting. In certain alternative embodiments, the processing may be performed in some different order or some steps may also be performed in parallel. It should be appreciated that in alternative embodiments the processing depicted in FIG. 7 may include a greater number or a lesser number of steps than those depicted in FIG. 7.

At step 710, an FHIR-compliance data structure that includes a set of sub-entity types of medication entity type, medical entities associated with the set of sub-entity types, and medical codes associated with the medical entities may be received. For example, in FIG. 5, the bridge for medication order pipeline 506 may receive an FHIR-compliance data structure generated by the medical entity detection and resolution pipeline 504. The FHIR-compliance data structure may be generated based on medication entity type by mapping medical entities to medical codes (an example of first-type medical codes) of RxNORM coding system (an example of a first medical coding system). Take the example in FIG. 3B and FIG. 5, the medical entities (an example of one or more tokens in an utterance) from an utterance ("Please order Tylenol to help alleviate Mary's headache using oral tablets, and let's start with 200 milligrams") are: Tylenol, oral, tablets, and 200 mg (after normalization). They are mapped to RxNORM codes, 12345, 22335 (not shown), 67890, and 12569, respectively, as shown in data structure 304 of FIG. 3B.

As discussed above in relation to FIG. 5, there are two options to generate the medication order information. The first option covers steps 730-732, and the second option covers steps 750-752.

For the first option, at step 730, the medical entities from the FHIR-compliance data structure may be identified. For example, the medical entities, Tylenol (in block 350), oral (not shown), tablets (in block 252), and 200 mg (in block 354) in the data structure 304 may be identified, and extracted.

At step 732, a search phrase using the identified medical entities may be generated. As discussed in FIG. 5, in some embodiments, the search phrase may be generated using a rule-based method and put in a particular order based on sub-entity types: ingredients, dose, route, dose form, frequency, refill, etc. Thus, the identified entities can be concatenated to form a search phrase as "Tylenol 200 mg oral tablets", where Tylenol is under ingredient sub-entity type, 200 mg is under dose sub-entity type, oral under route sub-entity type, and tablets under dose_form sub-entity type.

For the second option, at step 750, the medical codes associated with the medical entities from the FHIR-compliance data structure may be identified. Continuing with the above example, the RxNORM codes, 12345, 22335 (not shown), 67890, and 12569, which correspond to Tylenol, oral (not shown), tablets, and 200 mg, may be identified and extracted from the data structure 304 of FIG. 3B.

At step 752, each of the identified medical codes may be converted to a corresponding EHR system-specific medical code. For example, a particular EHR system may have its own EHR system-specific medical codes, such as IG-123 for ingredient type covering Tylenol, RT-456 for route type covering oral, DF-230 for dose_form type covering tablet, and DS-678 for dose type covering 200 mg. The identified RxNORM medical codes can then be converted into these EHR system-specific medical codes accordingly.

Example Cloud Service Provider Infrastructure (CSPI) Architectures

As noted above, infrastructure as a service (IaaS) is one particular type of cloud computing. IaaS can be configured to provide virtualized computing resources over a public network (e.g., the Internet). In an IaaS model, a cloud computing provider can host the infrastructure components (e.g., servers, storage devices, network nodes (e.g., hardware), deployment software, platform virtualization (e.g., a hypervisor layer), or the like). In some cases, an IaaS provider may also supply a variety of services to accompany those infrastructure components (example services include billing software, monitoring software, logging software, load balancing software, clustering software, etc.). Thus, as these services may be policy-driven, IaaS users may be able to implement policies to drive load balancing to maintain application availability and performance.

In some instances, IaaS customers may access resources and services through a wide area network (WAN), such as the Internet, and can use the cloud provider's services to install the remaining elements of an application stack. For example, the user can log in to the IaaS platform to create virtual machines (VMs), install operating systems (OSs) on each VM, deploy middleware such as databases, create storage buckets for workloads and backups, and even install enterprise software into that VM. Customers can then use the provider's services to perform various functions, including balancing network traffic, troubleshooting application issues, monitoring performance, managing disaster recovery, etc.

In most cases, a cloud computing model will require the participation of a cloud provider. The cloud provider may, but need not be, a third-party service that specializes in providing (e.g., offering, renting, selling) IaaS. An entity might also opt to deploy a private cloud, becoming its own provider of infrastructure services.

In some examples, IaaS deployment is the process of putting a new application, or a new version of an application, onto a prepared application server or the like. It may also include the process of preparing the server (e.g., installing libraries, daemons, etc.). This is often managed by the cloud provider, below the hypervisor layer (e.g., the servers, storage, network hardware, and virtualization). Thus, the customer may be responsible for handling (OS), middleware, and/or application deployment (e.g., on self-service virtual machines (e.g., that can be spun up on demand)) or the like.

In some examples, IaaS provisioning may refer to acquiring computers or virtual hosts for use, and even installing needed libraries or services on them. In most cases, deployment does not include provisioning, and the provisioning may need to be performed first.

In some cases, there are two different challenges for IaaS provisioning. First, there is the initial challenge of provisioning the initial set of infrastructure before anything is running. Second, there is the challenge of evolving the existing infrastructure (e.g., adding new services, changing services, removing services, etc.) once everything has been provisioned. In some cases, these two challenges may be addressed by enabling the configuration of the infrastructure to be defined declaratively. In other words, the infrastructure (e.g., what components are needed and how they interact) can be defined by one or more configuration files. Thus, the overall topology of the infrastructure (e.g., what resources depend on which, and how they each work together) can be described declaratively. In some instances, once the topology is defined, a workflow can be generated that creates and/or manages the different components described in the configuration files.

In some examples, an infrastructure may have many interconnected elements. For example, there may be one or more virtual private clouds (VPCs) (e.g., a potentially on-demand pool of configurable and/or shared computing resources), also known as a core network. In some examples, there may also be one or more inbound/outbound traffic group rules provisioned to define how the inbound and/or outbound traffic of the network will be set up and one or more virtual machines (VMs). Other infrastructure elements may also be provisioned, such as a load balancer, a database, or the like. As more and more infrastructure elements are desired and/or added, the infrastructure may incrementally evolve.

In some instances, continuous deployment techniques may be employed to enable deployment of infrastructure code across various virtual computing environments. Additionally, the described techniques can enable infrastructure management within these environments. In some examples, service teams can write code that is desired to be deployed to one or more, but often many, different production environments (e.g., across various different geographic locations, sometimes spanning the entire world). However, in some examples, the infrastructure on which the code will be deployed must first be set up. In some instances, the provisioning can be done manually, a provisioning tool may be utilized to provision the resources, and/or deployment tools may be utilized to deploy the code once the infrastructure is provisioned.

Figure 8:
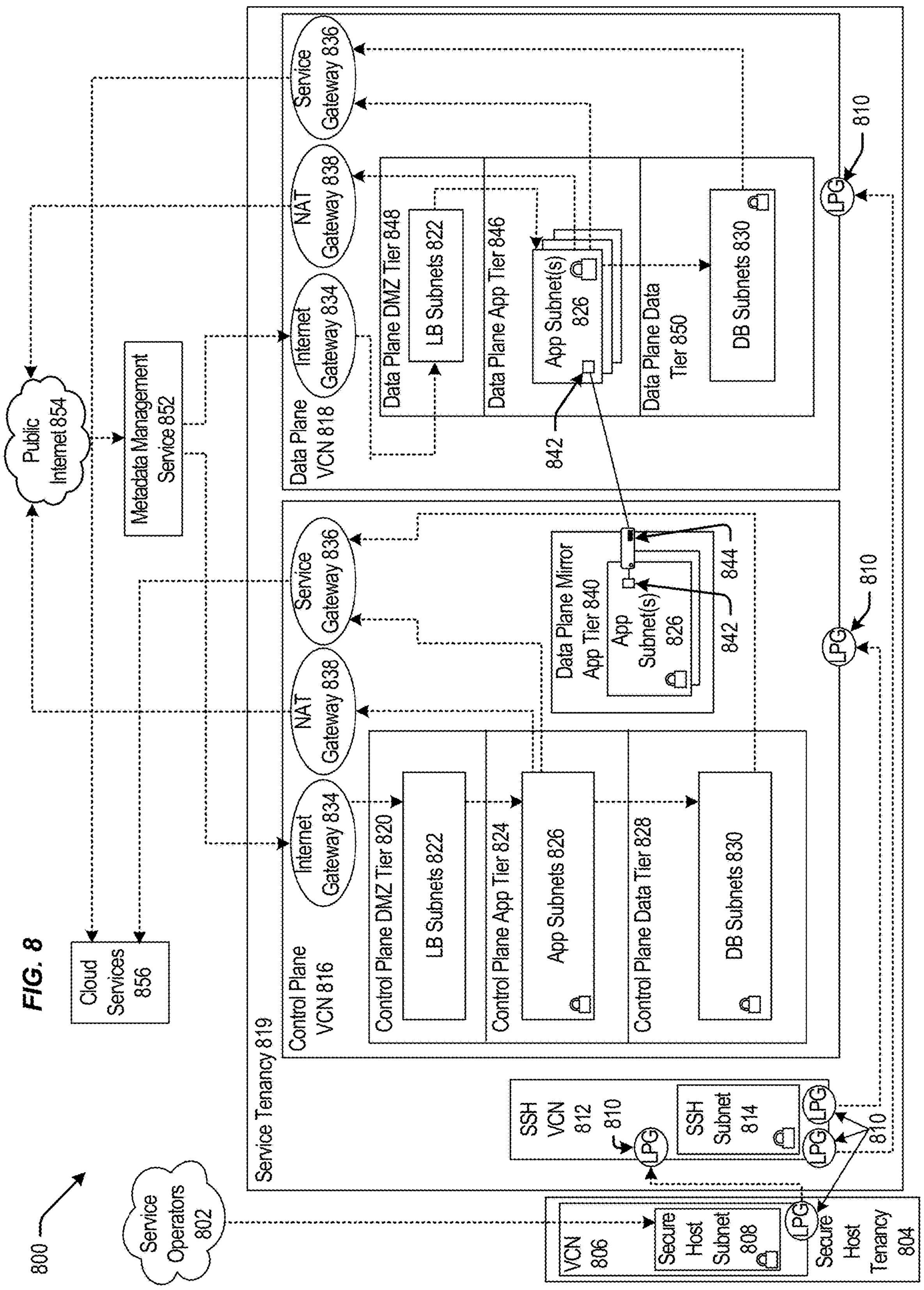
FIG. 8 is a block diagram illustrating one pattern for implementing a cloud infrastructure as a service system, according to at least one embodiment.

FIG. 8 is a block diagram 800 illustrating an example pattern of an IaaS architecture, according to at least one embodiment. Service operators 802 can be communicatively coupled to a secure host tenancy 804 that can include a virtual cloud network (VCN) 806 and a secure host subnet 808. In some examples, the service operators 802 may be using one or more client computing devices, which may be portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 8, Palm OS, and the like, and being Internet, e-mail, short message service (SMS), Blackberry®, or other communication protocol enabled. Alternatively, the client computing devices can be general purpose personal computers including, by way of example, personal computers and/or laptop computers running various versions of Microsoft Windows®, Apple Macintosh®, and/or Linux operating systems. The client computing devices can be workstation computers running any of a variety of commercially-available UNIX® or UNIX-like operating systems, including without limitation the variety of GNU/Linux operating systems, such as for example, Google Chrome OS. Alternatively, or in addition, client computing devices may be any other electronic device, such as a thin-client computer, an Internet-enabled gaming system (e.g., a Microsoft Xbox gaming console with or without a Kinect® gesture input device), and/or a personal messaging device, capable of communicating over a network that can access the VCN 806 and/or the Internet.

The VCN 806 can include a local peering gateway (LPG) 810 that can be communicatively coupled to a secure shell (SSH) VCN 812 via an LPG 810 contained in the SSH VCN 812. The SSH VCN 812 can include an SSH subnet 814, and the SSH VCN 812 can be communicatively coupled to a control plane VCN 816 via the LPG 810 contained in the control plane VCN 816. Also, the SSH VCN 812 can be communicatively coupled to a data plane VCN 818 via an LPG 810. The control plane VCN 816 and the data plane VCN 818 can be contained in a service tenancy 819 that can be owned and/or operated by the IaaS provider.

The control plane VCN 816 can include a control plane demilitarized zone (DMZ) tier 820 that acts as a perimeter network (e.g., portions of a corporate network between the corporate intranet and external networks). The DMZ-based servers may have restricted responsibilities and help keep breaches contained. Additionally, the DMZ tier 820 can include one or more load balancer (LB) subnet(s) 822, a control plane app tier 824 that can include app subnet(s) 826, a control plane data tier 828 that can include database (DB) subnet(s) 830 (e.g., frontend DB subnet(s) and/or backend DB subnet(s)). The LB subnet(s) 822 contained in the control plane DMZ tier 820 can be communicatively coupled to the app subnet(s) 826 contained in the control plane app tier 824 and an Internet gateway 834 that can be contained in the control plane VCN 816, and the app subnet(s) 826 can be communicatively coupled to the DB subnet(s) 830 contained in the control plane data tier 828 and a service gateway 836 and a network address translation (NAT) gateway 838. The control plane VCN 816 can include the service gateway 836 and the NAT gateway 838.

The control plane VCN 816 can include a data plane mirror app tier 840 that can include app subnet(s) 826. The app subnet(s) 826 contained in the data plane mirror app tier 840 can include a virtual network interface controller (VNIC) 842 that can execute a compute instance 844. The compute instance 844 can communicatively couple the app subnet(s) 826 of the data plane mirror app tier 840 to app subnet(s) 826 that can be contained in a data plane app tier 846.

The data plane VCN 818 can include the data plane app tier 846, a data plane DMZ tier 848, and a data plane data tier 850. The data plane DMZ tier 848 can include LB subnet(s) 822 that can be communicatively coupled to the app subnet(s) 826 of the data plane app tier 846 and the Internet gateway 834 of the data plane VCN 818. The app subnet(s) 826 can be communicatively coupled to the service gateway 836 of the data plane VCN 818 and the NAT gateway 838 of the data plane VCN 818. The data plane data tier 850 can also include the DB subnet(s) 830 that can be communicatively coupled to the app subnet(s) 826 of the data plane app tier 846.

The Internet gateway 834 of the control plane VCN 816 and of the data plane VCN 818 can be communicatively coupled to a metadata management service 852 that can be communicatively coupled to public Internet 854. Public Internet 854 can be communicatively coupled to the NAT gateway 838 of the control plane VCN 816 and of the data plane VCN 818. The service gateway 836 of the control plane VCN 816 and of the data plane VCN 818 can be communicatively coupled to cloud services 856.

In some examples, the service gateway 836 of the control plane VCN 816 or of the data plane VCN 818 can make application programming interface (API) calls to cloud services 856 without going through public Internet 854. The API calls to cloud services 856 from the service gateway 836 can be one-way: the service gateway 836 can make API calls to cloud services 856, and cloud services 856 can send requested data to the service gateway 836. But, cloud services 856 may not initiate API calls to the service gateway 836.

In some examples, the secure host tenancy 804 can be directly connected to the service tenancy 819, which may be otherwise isolated. The secure host subnet 808 can communicate with the SSH subnet 814 through an LPG 810 that may enable two-way communication over an otherwise isolated system. Connecting the secure host subnet 808 to the SSH subnet 814 may give the secure host subnet 808 access to other entities within the service tenancy 819.

The control plane VCN 816 may allow users of the service tenancy 819 to set up or otherwise provision desired resources. Desired resources provisioned in the control plane VCN 816 may be deployed or otherwise used in the data plane VCN 818. In some examples, the control plane VCN 816 can be isolated from the data plane VCN 818, and the data plane mirror app tier 840 of the control plane VCN 816 can communicate with the data plane app tier 846 of the data plane VCN 818 via VNICs 842 that can be contained in the data plane mirror app tier 840 and the data plane app tier 846.

In some examples, users of the system, or customers, can make requests, for example create, read, update, or delete (CRUD) operations, through public Internet 854 that can communicate the requests to the metadata management service 852. The metadata management service 852 can communicate the request to the control plane VCN 816 through the Internet gateway 834. The request can be received by the LB subnet(s) 822 contained in the control plane DMZ tier 820. The LB subnet(s) 822 may determine that the request is valid, and in response to this determination, the LB subnet(s) 822 can transmit the request to app subnet(s) 826 contained in the control plane app tier 824. If the request is validated and requires a call to public Internet 854, the call to public Internet 854 may be transmitted to the NAT gateway 838 that can make the call to public Internet 854. Metadata that may be desired to be stored by the request can be stored in the DB subnet(s) 830.

In some examples, the data plane mirror app tier 840 can facilitate direct communication between the control plane VCN 816 and the data plane VCN 818. For example, changes, updates, or other suitable modifications to configuration may be desired to be applied to the resources contained in the data plane VCN 818. Via a VNIC 842, the control plane VCN 816 can directly communicate with, and can thereby execute the changes, updates, or other suitable modifications to configuration to, resources contained in the data plane VCN 818.

In some embodiments, the control plane VCN 816 and the data plane VCN 818 can be contained in the service tenancy 819. In this case, the user, or the customer, of the system may not own or operate either the control plane VCN 816 or the data plane VCN 818. Instead, the IaaS provider may own or operate the control plane VCN 816 and the data plane VCN 818, both of which may be contained in the service tenancy 819. This embodiment can enable isolation of networks that may prevent users or customers from interacting with other users', or other customers', resources. Also, this embodiment may allow users or customers of the system to store databases privately without needing to rely on public Internet 854, which may not have a desired level of threat prevention, for storage.

In other embodiments, the LB subnet(s) 822 contained in the control plane VCN 816 can be configured to receive a signal from the service gateway 836. In this embodiment, the control plane VCN 816 and the data plane VCN 818 may be configured to be called by a customer of the IaaS provider without calling public Internet 854. Customers of the IaaS provider may desire this embodiment since database(s) that the customers use may be controlled by the IaaS provider and may be stored on the service tenancy 819, which may be isolated from public Internet 854.

Figure 9:
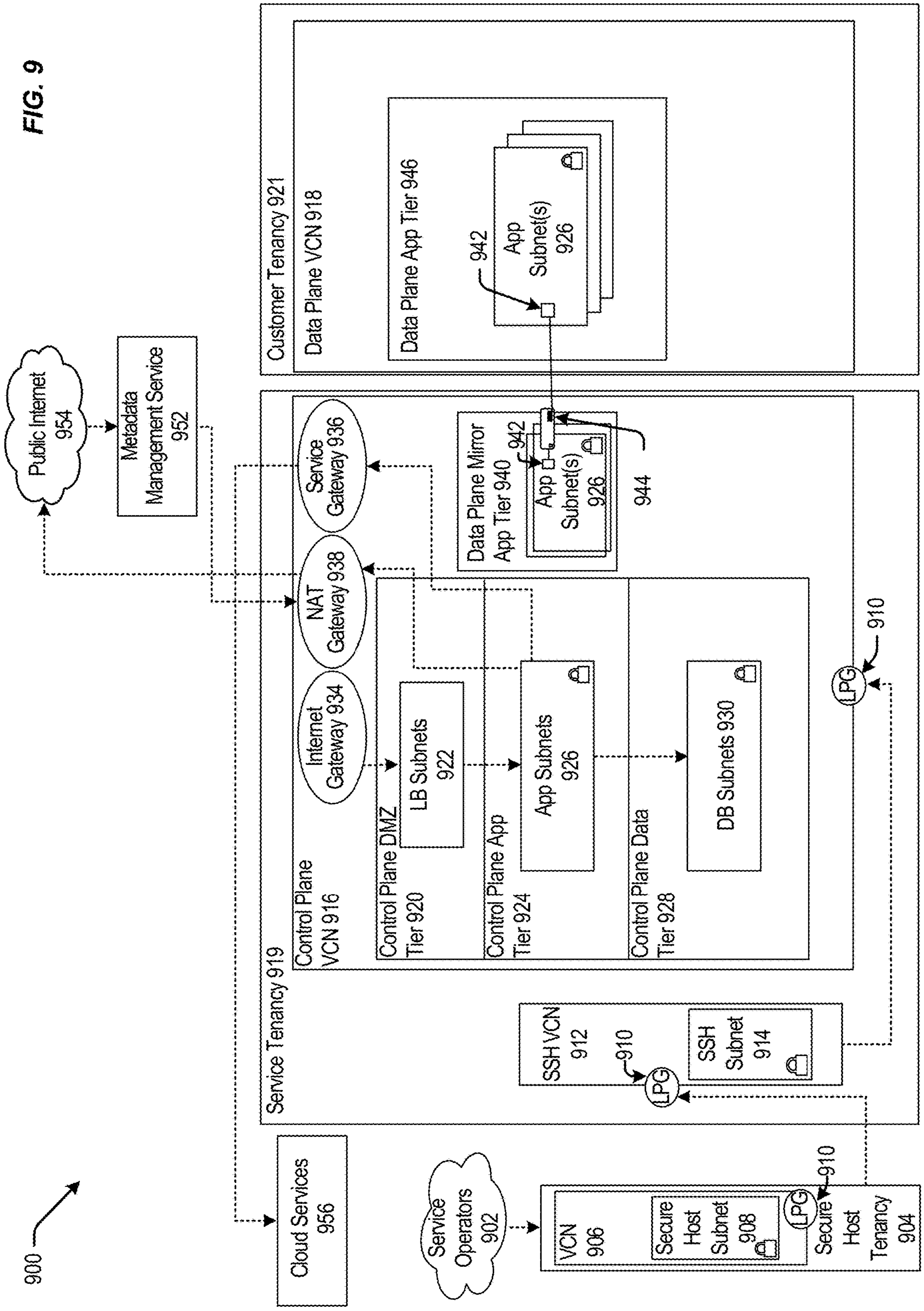
FIG. 9 is a block diagram illustrating another pattern for implementing a cloud infrastructure as a service system, according to at least one embodiment.

FIG. 9 is a block diagram 900 illustrating another example pattern of an IaaS architecture, according to at least one embodiment. Service operators 902 (e.g., service operators 802 of FIG. 8) can be communicatively coupled to a secure host tenancy 904 (e.g., the secure host tenancy 804 of FIG. 8) that can include a virtual cloud network (VCN) 906 (e.g., the VCN 806 of FIG. 8) and a secure host subnet 908 (e.g., the secure host subnet 808 of FIG. 8). The VCN 906 can include a local peering gateway (LPG) 910 (e.g., the LPG 810 of FIG. 8) that can be communicatively coupled to a secure shell (SSH) VCN 912 (e.g., the SSH VCN 812 of FIG. 8) via an LPG 810 contained in the SSH VCN 912. The SSH VCN 912 can include an SSH subnet 914 (e.g., the SSH subnet 814 of FIG. 8), and the SSH VCN 912 can be communicatively coupled to a control plane VCN 916 (e.g., the control plane VCN 816 of FIG. 8) via an LPG 910 contained in the control plane VCN 916. The control plane VCN 916 can be contained in a service tenancy 919 (e.g., the service tenancy 819 of FIG. 8), and the data plane VCN 918 (e.g., the data plane VCN 818 of FIG. 8) can be contained in a customer tenancy 921 that may be owned or operated by users, or customers, of the system.

The control plane VCN 916 can include a control plane DMZ tier 920 (e.g., the control plane DMZ tier 820 of FIG. 8) that can include LB subnet(s) 922 (e.g., LB subnet(s) 822 of FIG. 8), a control plane app tier 924 (e.g., the control plane app tier 824 of FIG. 8) that can include app subnet(s) 926 (e.g., app subnet(s) 826 of FIG. 8), a control plane data tier 928 (e.g., the control plane data tier 828 of FIG. 8) that can include database (DB) subnet(s) 930 (e.g., similar to DB subnet(s) 830 of FIG. 8). The LB subnet(s) 922 contained in the control plane DMZ tier 920 can be communicatively coupled to the app subnet(s) 926 contained in the control plane app tier 924 and an Internet gateway 934 (e.g., the Internet gateway 834 of FIG. 8) that can be contained in the control plane VCN 916, and the app subnet(s) 926 can be communicatively coupled to the DB subnet(s) 930 contained in the control plane data tier 928 and a service gateway 936 (e.g., the service gateway 836 of FIG. 8) and a network address translation (NAT) gateway 938 (e.g., the NAT gateway 838 of FIG. 8). The control plane VCN 916 can include the service gateway 936 and the NAT gateway 938.

The control plane VCN 916 can include a data plane mirror app tier 940 (e.g., the data plane mirror app tier 840 of FIG. 8) that can include app subnet(s) 926. The app subnet(s) 926 contained in the data plane mirror app tier 940 can include a virtual network interface controller (VNIC) 942 (e.g., the VNIC of 842) that can execute a compute instance 944 (e.g., similar to the compute instance 844 of FIG. 8). The compute instance 944 can facilitate communication between the app subnet(s) 926 of the data plane mirror app tier 940 and the app subnet(s) 926 that can be contained in a data plane app tier 946 (e.g., the data plane app tier 846 of FIG. 8) via the VNIC 942 contained in the data plane mirror app tier 940 and the VNIC 942 contained in the data plane app tier 946.

The Internet gateway 934 contained in the control plane VCN 916 can be communicatively coupled to a metadata management service 952 (e.g., the metadata management service 852 of FIG. 8) that can be communicatively coupled to public Internet 954 (e.g., public Internet 854 of FIG. 8). Public Internet 954 can be communicatively coupled to the NAT gateway 938 contained in the control plane VCN 916. The service gateway 936 contained in the control plane VCN 916 can be communicatively coupled to cloud services 956 (e.g., cloud services 856 of FIG. 8).

In some examples, the data plane VCN 918 can be contained in the customer tenancy 921. In this case, the IaaS provider may provide the control plane VCN 916 for each customer, and the IaaS provider may, for each customer, set up a unique compute instance 944 that is contained in the service tenancy 919. Each compute instance 944 may allow communication between the control plane VCN 916, contained in the service tenancy 919, and the data plane VCN 918 that is contained in the customer tenancy 921. The compute instance 944 may allow resources, that are provisioned in the control plane VCN 916 that is contained in the service tenancy 919, to be deployed or otherwise used in the data plane VCN 918 that is contained in the customer tenancy 921.

In other examples, the customer of the IaaS provider may have databases that live in the customer tenancy 921. In this example, the control plane VCN 916 can include the data plane mirror app tier 940 that can include app subnet(s) 926. The data plane mirror app tier 940 can reside in the data plane VCN 918, but the data plane mirror app tier 940 may not live in the data plane VCN 918. That is, the data plane mirror app tier 940 may have access to the customer tenancy 921, but the data plane mirror app tier 940 may not exist in the data plane VCN 918 or be owned or operated by the customer of the IaaS provider. The data plane mirror app tier 940 may be configured to make calls to the data plane VCN 918 but may not be configured to make calls to any entity contained in the control plane VCN 916. The customer may desire to deploy or otherwise use resources in the data plane VCN 918 that are provisioned in the control plane VCN 916, and the data plane mirror app tier 940 can facilitate the desired deployment, or other usage of resources, of the customer.

In some embodiments, the customer of the IaaS provider can apply filters to the data plane VCN 918. In this embodiment, the customer can determine what the data plane VCN 918 can access, and the customer may restrict access to public Internet 954 from the data plane VCN 918. The IaaS provider may not be able to apply filters or otherwise control access of the data plane VCN 918 to any outside networks or databases. Applying filters and controls by the customer onto the data plane VCN 918, contained in the customer tenancy 921, can help isolate the data plane VCN 918 from other customers and from public Internet 954.

In some embodiments, cloud services 956 can be called by the service gateway 936 to access services that may not exist on public Internet 954, on the control plane VCN 916, or on the data plane VCN 918. The connection between cloud services 956 and the control plane VCN 916 or the data plane VCN 918 may not be live or continuous. Cloud services 956 may exist on a different network owned or operated by the IaaS provider. Cloud services 956 may be configured to receive calls from the service gateway 936 and may be configured to not receive calls from public Internet 954. Some cloud services 956 may be isolated from other cloud services 956, and the control plane VCN 916 may be isolated from cloud services 956 that may not be in the same region as the control plane VCN 916. For example, the control plane VCN 916 may be located in "Region 1," and cloud service "Deployment 8," may be located in Region 1 and in "Region 2." If a call to Deployment 8 is made by the service gateway 936 contained in the control plane VCN 916 located in Region 1, the call may be transmitted to Deployment 8 in Region 1. In this example, the control plane VCN 916, or Deployment 8 in Region 1, may not be communicatively coupled to, or otherwise in communication with, Deployment 8 in Region 2.

Figure 10:
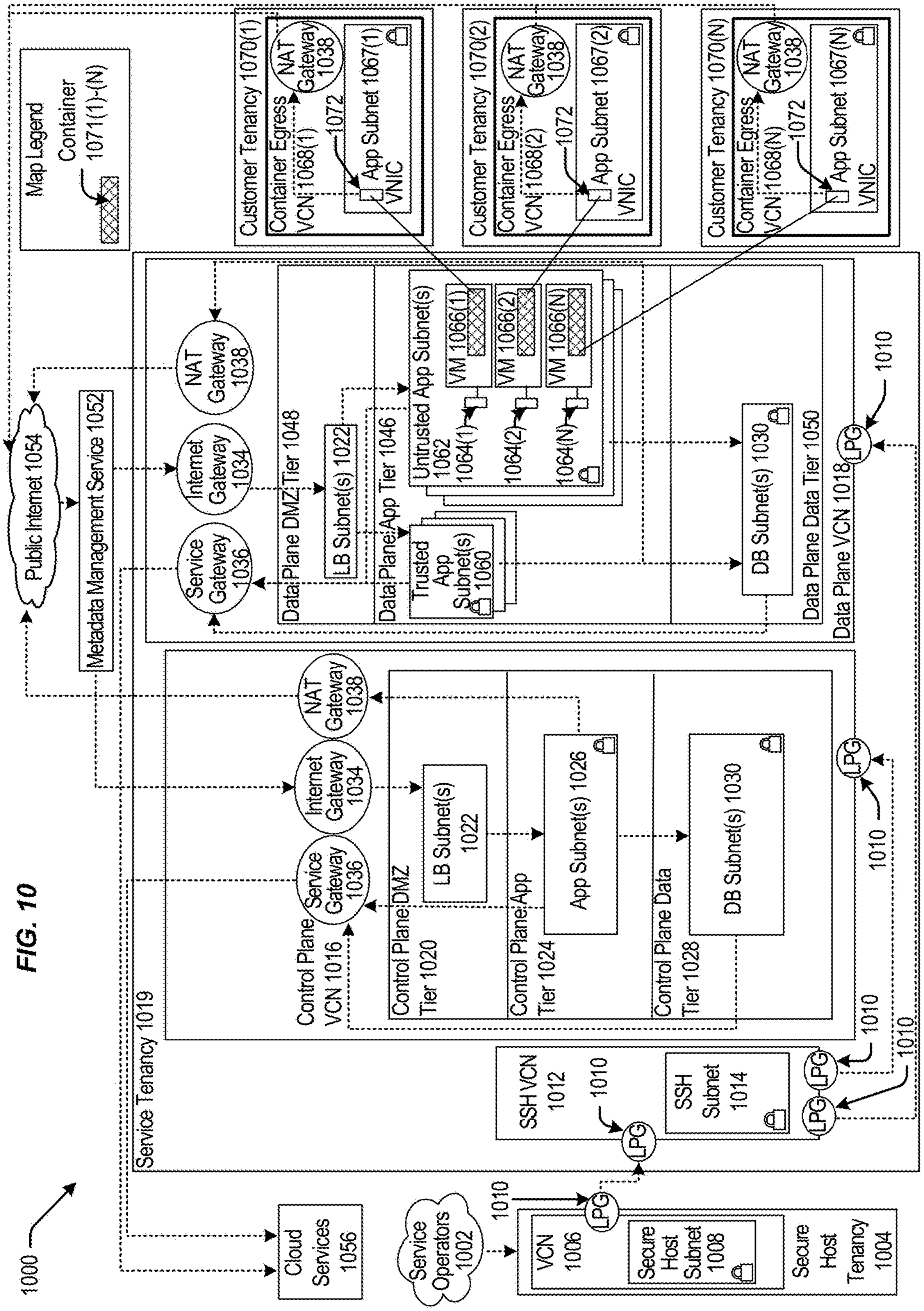
FIG. 10 is a block diagram illustrating another pattern for implementing a cloud infrastructure as a service system, according to at least one embodiment.

FIG. 10 is a block diagram 1000 illustrating another example pattern of an IaaS architecture, according to at least one embodiment. Service operators 1002 (e.g., service operators 802 of FIG. 8) can be communicatively coupled to a secure host tenancy 1004 (e.g., the secure host tenancy 804 of FIG. 8) that can include a virtual cloud network (VCN) 1006 (e.g., the VCN 806 of FIG. 8) and a secure host subnet 1008 (e.g., the secure host subnet 808 of FIG. 8). The VCN 1006 can include an LPG 1010 (e.g., the LPG 810 of FIG. 8) that can be communicatively coupled to an SSH VCN 1012 (e.g., the SSH VCN 812 of FIG. 8) via an LPG 1010 contained in the SSH VCN 1012. The SSH VCN 1012 can include an SSH subnet 1014 (e.g., the SSH subnet 814 of FIG. 8), and the SSH VCN 1012 can be communicatively coupled to a control plane VCN 1016 (e.g., the control plane VCN 816 of FIG. 8) via an LPG 1010 contained in the control plane VCN 1016 and to a data plane VCN 1018 (e.g., the data plane 818 of FIG. 8) via an LPG 1010 contained in the data plane VCN 1018. The control plane VCN 1016 and the data plane VCN 1018 can be contained in a service tenancy 1019 (e.g., the service tenancy 819 of FIG. 8).

The control plane VCN 1016 can include a control plane DMZ tier 1020 (e.g., the control plane DMZ tier 820 of FIG. 8) that can include load balancer (LB) subnet(s) 1022 (e.g., LB subnet(s) 822 of FIG. 8), a control plane app tier 1024 (e.g., the control plane app tier 824 of FIG. 8) that can include app subnet(s) 1026 (e.g., similar to app subnet(s) 826 of FIG. 8), a control plane data tier 1028 (e.g., the control plane data tier 828 of FIG. 8) that can include DB subnet(s) 1030. The LB subnet(s) 1022 contained in the control plane DMZ tier 1020 can be communicatively coupled to the app subnet(s) 1026 contained in the control plane app tier 1024 and to an Internet gateway 1034 (e.g., the Internet gateway 834 of FIG. 8) that can be contained in the control plane VCN 1016, and the app subnet(s) 1026 can be communicatively coupled to the DB subnet(s) 1030 contained in the control plane data tier 1028 and to a service gateway 1036 (e.g., the service gateway of FIG. 8) and a network address translation (NAT) gateway 1038 (e.g., the NAT gateway 838 of FIG. 8). The control plane VCN 1016 can include the service gateway 1036 and the NAT gateway 1038.

The data plane VCN 1018 can include a data plane app tier 1046 (e.g., the data plane app tier 846 of FIG. 8), a data plane DMZ tier 1048 (e.g., the data plane DMZ tier 848 of FIG. 8), and a data plane data tier 1050 (e.g., the data plane data tier 850 of FIG. 8). The data plane DMZ tier 1048 can include LB subnet(s) 1022 that can be communicatively coupled to trusted app subnet(s) 1060 and untrusted app subnet(s) 1062 of the data plane app tier 1046 and the Internet gateway 1034 contained in the data plane VCN 1018. The trusted app subnet(s) 1060 can be communicatively coupled to the service gateway 1036 contained in the data plane VCN 1018, the NAT gateway 1038 contained in the data plane VCN 1018, and DB subnet(s) 1030 contained in the data plane data tier 1050. The untrusted app subnet(s) 1062 can be communicatively coupled to the service gateway 1036 contained in the data plane VCN 1018 and DB subnet(s) 1030 contained in the data plane data tier 1050. The data plane data tier 1050 can include DB subnet(s) 1030 that can be communicatively coupled to the service gateway 1036 contained in the data plane VCN 1018.

The untrusted app subnet(s) 1062 can include one or more primary VNICs 1064(1)-(N) that can be communicatively coupled to tenant virtual machines (VMs) 1066(1)-(N). Each tenant VM 1066(1)-(N) can be communicatively coupled to a respective app subnet 1067(1)-(N) that can be contained in respective container egress VCNs 1068(1)-(N) that can be contained in respective customer tenancies 1070(1)-(N). Respective secondary VNICs 1072(1)-(N) can facilitate communication between the untrusted app subnet(s) 1062 contained in the data plane VCN 1018 and the app subnet contained in the container egress VCNs 1068(1)-(N). Each container egress VCNs 1068(1)-(N) can include a NAT gateway 1038 that can be communicatively coupled to public Internet 1054 (e.g., public Internet 854 of FIG. 8).

The Internet gateway 1034 contained in the control plane VCN 1016 and contained in the data plane VCN 1018 can be communicatively coupled to a metadata management service 1052 (e.g., the metadata management system 852 of FIG. 8) that can be communicatively coupled to public Internet 1054. Public Internet 1054 can be communicatively coupled to the NAT gateway 1038 contained in the control plane VCN 1016 and contained in the data plane VCN 1018. The service gateway 1036 contained in the control plane VCN 1016 and contained in the data plane VCN 1018 can be communicatively coupled to cloud services 1056.

In some embodiments, the data plane VCN 1018 can be integrated with customer tenancies 1070. This integration can be useful or desirable for customers of the IaaS provider in some cases such as a case that may desire support when executing code. The customer may provide code to run that may be destructive, may communicate with other customer resources, or may otherwise cause undesirable effects. In response to this, the IaaS provider may determine whether to run code given to the IaaS provider by the customer.

In some examples, the customer of the IaaS provider may grant temporary network access to the IaaS provider and request a function to be attached to the data plane app tier 1046. Code to run the function may be executed in the VMs 1066(1)-(N), and the code may not be configured to run anywhere else on the data plane VCN 1018. Each VM 1066(1)-(N) may be connected to one customer tenancy 1070. Respective containers 1071(1)-(N) contained in the VMs 1066(1)-(N) may be configured to run the code. In this case, there can be a dual isolation (e.g., the containers 1071(1)-(N) running code, where the containers 1071(1)-(N) may be contained in at least the VM 1066(1)-(N) that are contained in the untrusted app subnet(s) 1062), which may help prevent incorrect or otherwise undesirable code from damaging the network of the IaaS provider or from damaging a network of a different customer. The containers 1071(1)-(N) may be communicatively coupled to the customer tenancy 1070 and may be configured to transmit or receive data from the customer tenancy 1070. The containers 1071(1)-(N) may not be configured to transmit or receive data from any other entity in the data plane VCN 1018. Upon completion of running the code, the IaaS provider may kill or otherwise dispose of the containers 1071(1)-(N).

In some embodiments, the trusted app subnet(s) 1060 may run code that may be owned or operated by the IaaS provider. In this embodiment, the trusted app subnet(s) 1060 may be communicatively coupled to the DB subnet(s) 1030 and be configured to execute CRUD operations in the DB subnet(s) 1030. The untrusted app subnet(s) 1062 may be communicatively coupled to the DB subnet(s) 1030, but in this embodiment, the untrusted app subnet(s) may be configured to execute read operations in the DB subnet(s) 1030. The containers 1071(1)-(N) that can be contained in the VM 1066(1)-(N) of each customer and that may run code from the customer may not be communicatively coupled with the DB subnet(s) 1030.

In other embodiments, the control plane VCN 1016 and the data plane VCN 1018 may not be directly communicatively coupled. In this embodiment, there may be no direct communication between the control plane VCN 1016 and the data plane VCN 1018. However, communication can occur indirectly through at least one method. An LPG 1010 may be established by the IaaS provider that can facilitate communication between the control plane VCN 1016 and the data plane VCN 1018. In another example, the control plane VCN 1016 or the data plane VCN 1018 can make a call to cloud services 1056 via the service gateway 1036. For example, a call to cloud services 1056 from the control plane VCN 1016 can include a request for a service that can communicate with the data plane VCN 1018.

Figure 11:
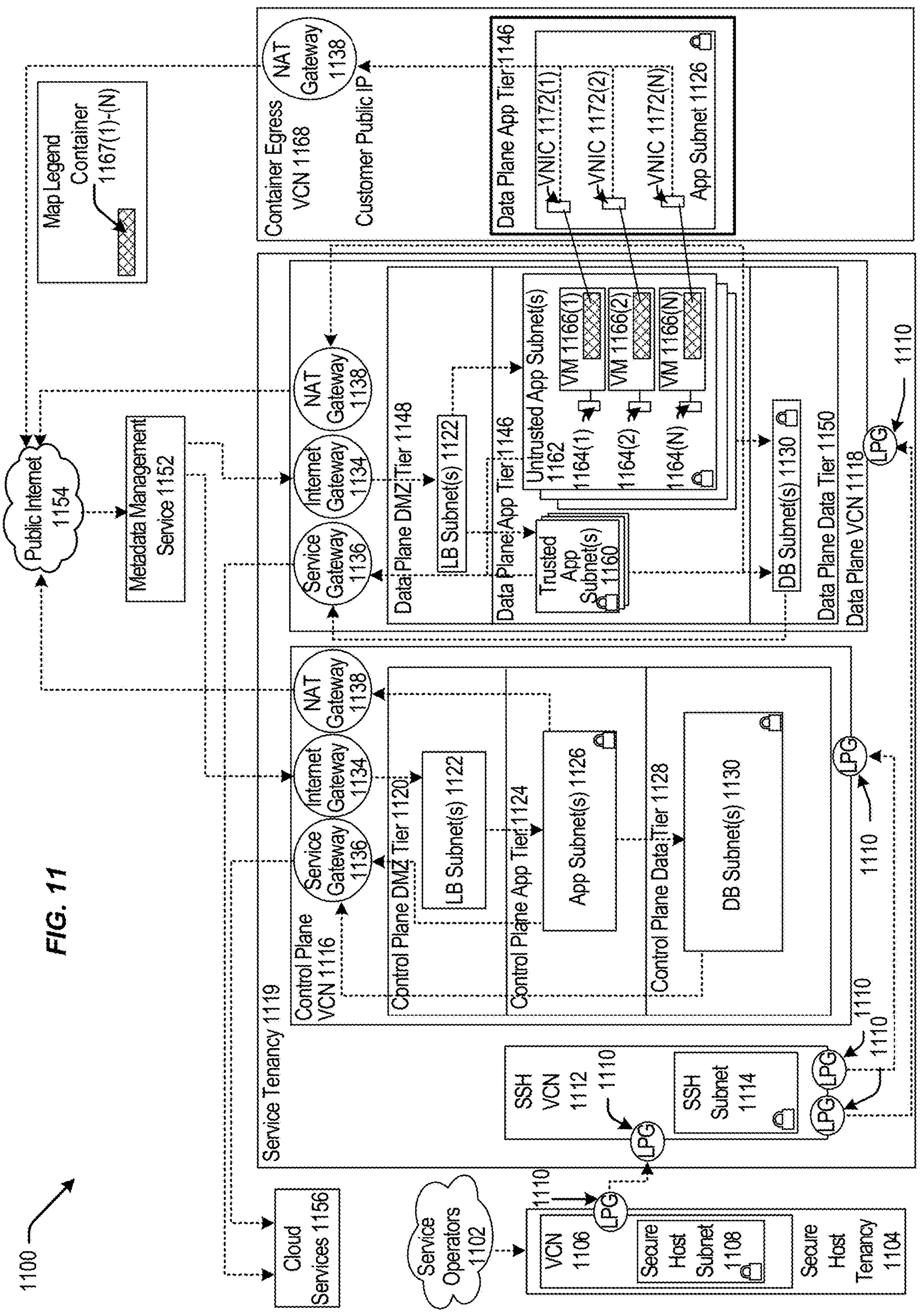
FIG. 11 is a block diagram illustrating another pattern for implementing a cloud infrastructure as a service system, according to at least one embodiment.

FIG. 11 is a block diagram 1100 illustrating another example pattern of an IaaS architecture, according to at least one embodiment. Service operators 1102 (e.g., service operators 802 of FIG. 8) can be communicatively coupled to a secure host tenancy 1104 (e.g., the secure host tenancy 804 of FIG. 8) that can include a virtual cloud network (VCN) 1106 (e.g., the VCN 806 of FIG. 8) and a secure host subnet 1108 (e.g., the secure host subnet 808 of FIG. 8). The VCN 1106 can include an LPG 1110 (e.g., the LPG 810 of FIG. 8) that can be communicatively coupled to an SSH VCN 1112 (e.g., the SSH VCN 812 of FIG. 8) via an LPG 1110 contained in the SSH VCN 1112. The SSH VCN 1112 can include an SSH subnet 1114 (e.g., the SSH subnet 814 of FIG. 8), and the SSH VCN 1112 can be communicatively coupled to a control plane VCN 1116 (e.g., the control plane VCN 816 of FIG. 8) via an LPG 1110 contained in the control plane VCN 1116 and to a data plane VCN 1118 (e.g., the data plane 818 of FIG. 8) via an LPG 1110 contained in the data plane VCN 1118. The control plane VCN 1116 and the data plane VCN 1118 can be contained in a service tenancy 1119 (e.g., the service tenancy 819 of FIG. 8).

The control plane VCN 1116 can include a control plane DMZ tier 1120 (e.g., the control plane DMZ tier 820 of FIG. 8) that can include LB subnet(s) 1122 (e.g., LB subnet(s) 822 of FIG. 8), a control plane app tier 1124 (e.g., the control plane app tier 824 of FIG. 8) that can include app subnet(s) 1126 (e.g., app subnet(s) 826 of FIG. 8), a control plane data tier 1128 (e.g., the control plane data tier 828 of FIG. 8) that can include DB subnet(s) 1130 (e.g., DB subnet(s) 1030 of FIG. 10). The LB subnet(s) 1122 contained in the control plane DMZ tier 1120 can be communicatively coupled to the app subnet(s) 1126 contained in the control plane app tier 1124 and to an Internet gateway 1134 (e.g., the Internet gateway 834 of FIG. 8) that can be contained in the control plane VCN 1116, and the app subnet(s) 1126 can be communicatively coupled to the DB subnet(s) 1130 contained in the control plane data tier 1128 and to a service gateway 1136 (e.g., the service gateway of FIG. 8) and a network address translation (NAT) gateway 1138 (e.g., the NAT gateway 838 of FIG. 8). The control plane VCN 1116 can include the service gateway 1136 and the NAT gateway 1138.

The data plane VCN 1118 can include a data plane app tier 1146 (e.g., the data plane app tier 846 of FIG. 8), a data plane DMZ tier 1148 (e.g., the data plane DMZ tier 848 of FIG. 8), and a data plane data tier 1150 (e.g., the data plane data tier 850 of FIG. 8). The data plane DMZ tier 1148 can include LB subnet(s) 1122 that can be communicatively coupled to trusted app subnet(s) 1160 (e.g., trusted app subnet(s) 1060 of FIG. 10) and untrusted app subnet(s) 1162 (e.g., untrusted app subnet(s) 1062 of FIG. 10) of the data plane app tier 1146 and the Internet gateway 1134 contained in the data plane VCN 1118. The trusted app subnet(s) 1160 can be communicatively coupled to the service gateway 1136 contained in the data plane VCN 1118, the NAT gateway 1138 contained in the data plane VCN 1118, and DB subnet(s) 1130 contained in the data plane data tier 1150. The untrusted app subnet(s) 1162 can be communicatively coupled to the service gateway 1136 contained in the data plane VCN 1118 and DB subnet(s) 1130 contained in the data plane data tier 1150. The data plane data tier 1150 can include DB subnet(s) 1130 that can be communicatively coupled to the service gateway 1136 contained in the data plane VCN 1118.

The untrusted app subnet(s) 1162 can include primary VNICs 1164(1)-(N) that can be communicatively coupled to tenant virtual machines (VMs) 1166(1)-(N) residing within the untrusted app subnet(s) 1162. Each tenant VM 1166(1)-(N) can run code in a respective container 1167(1)-(N), and be communicatively coupled to an app subnet 1126 that can be contained in a data plane app tier 1146 that can be contained in a container egress VCN 1168. Respective secondary VNICs 1172(1)-(N) can facilitate communication between the untrusted app subnet(s) 1162 contained in the data plane VCN 1118 and the app subnet contained in the container egress VCN 1168. The container egress VCN can include a NAT gateway 1138 that can be communicatively coupled to public Internet 1154 (e.g., public Internet 854 of FIG. 8).

The Internet gateway 1134 contained in the control plane VCN 1116 and contained in the data plane VCN 1118 can be communicatively coupled to a metadata management service 1152 (e.g., the metadata management system 852 of FIG. 8) that can be communicatively coupled to public Internet 1154. Public Internet 1154 can be communicatively coupled to the NAT gateway 1138 contained in the control plane VCN 1116 and contained in the data plane VCN 1118. The service gateway 1136 contained in the control plane VCN 1116 and contained in the data plane VCN 1118 can be communicatively coupled to cloud services 1156.

In some examples, the pattern illustrated by the architecture of block diagram 1100 of FIG. 11 may be considered an exception to the pattern illustrated by the architecture of block diagram 1000 of FIG. 10 and may be desirable for a customer of the IaaS provider if the IaaS provider cannot directly communicate with the customer (e.g., a disconnected region). The respective containers 1167(1)-(N) that are contained in the VMs 1166(1)-(N) for each customer can be accessed in real-time by the customer. The containers 1167(1)-(N) may be configured to make calls to respective secondary VNICs 1172(1)-(N) contained in app subnet(s) 1126 of the data plane app tier 1146 that can be contained in the container egress VCN 1168. The secondary VNICs 1172(1)-(N) can transmit the calls to the NAT gateway 1138 that may transmit the calls to public Internet 1154. In this example, the containers 1167(1)-(N) that can be accessed in real-time by the customer can be isolated from the control plane VCN 1116 and can be isolated from other entities contained in the data plane VCN 1118. The containers 1167(1)-(N) may also be isolated from resources from other customers.

In other examples, the customer can use the containers 1167(1)-(N) to call cloud services 1156. In this example, the customer may run code in the containers 1167(1)-(N) that requests a service from cloud services 1156. The containers 1167(1)-(N) can transmit this request to the secondary VNICs 1172(1)-(N) that can transmit the request to the NAT gateway that can transmit the request to public Internet 1154. Public Internet 1154 can transmit the request to LB subnet(s) 1122 contained in the control plane VCN 1116 via the Internet gateway 1134. In response to determining the request is valid, the LB subnet(s) can transmit the request to app subnet(s) 1126 that can transmit the request to cloud services 1156 via the service gateway 1136.

It should be appreciated that IaaS architectures 800, 900, 1000, 1100 depicted in the figures may have other components than those depicted. Further, the embodiments shown in the figures are only some examples of a cloud infrastructure system that may incorporate an embodiment of the disclosure. In some other embodiments, the IaaS systems may have more or fewer components than shown in the figures, may combine two or more components, or may have a different configuration or arrangement of components.

In certain embodiments, the IaaS systems described herein may include a suite of applications, middleware, and database service offerings that are delivered to a customer in a self-service, subscription-based, elastically scalable, reliable, highly available, and secure manner. An example of such an IaaS system is the Oracle Cloud Infrastructure (OCI) provided by the present assignee.

Figure 12:
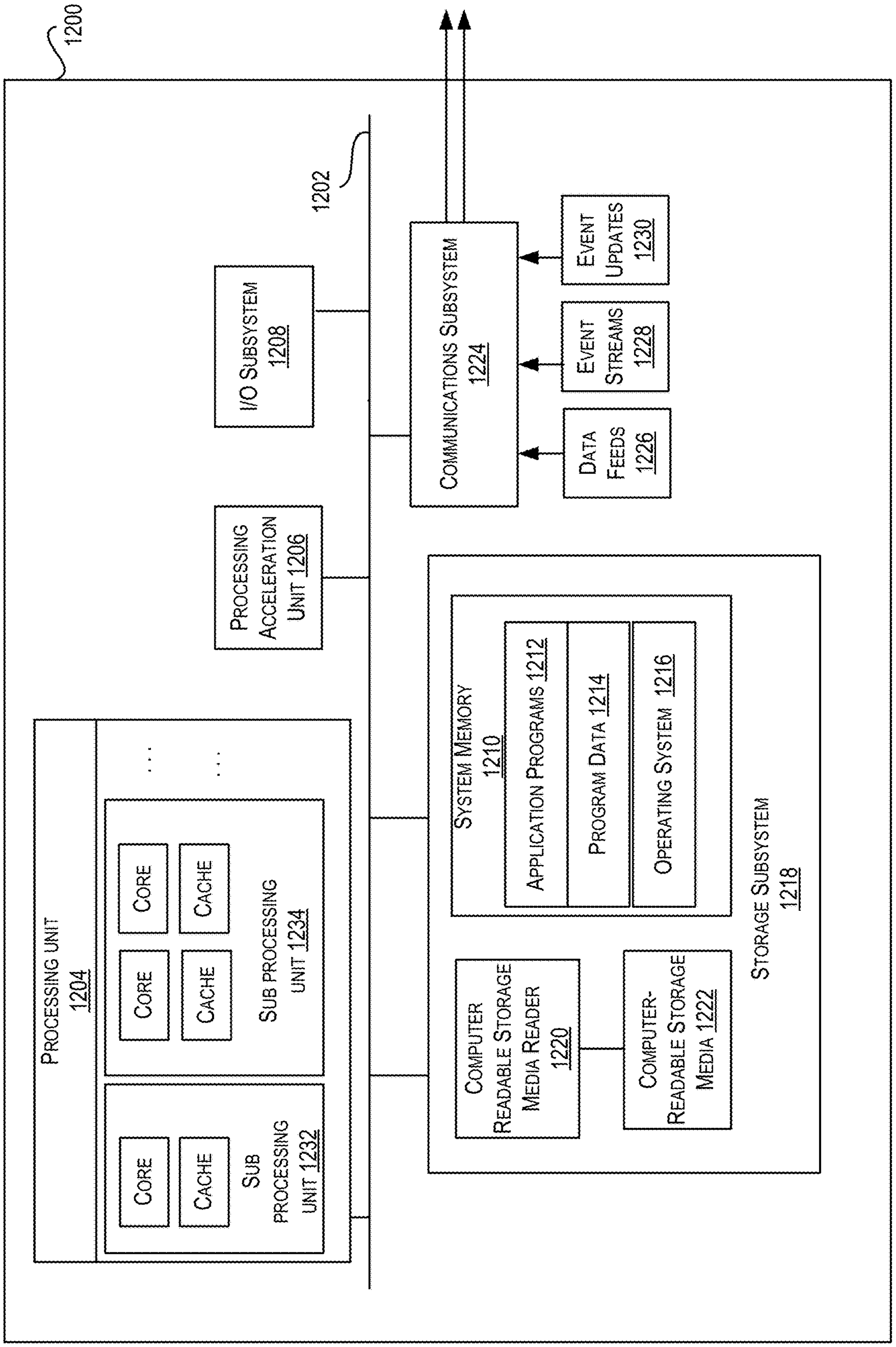
FIG. 12 is a block diagram illustrating an example computer system, according to at least one embodiment.

FIG. 12 illustrates an example computer system 1200, in which various embodiments may be implemented. The system 1200 may be used to implement any of the computer systems described above. As shown in the figure, computer system 1200 includes a processing unit 1204 that communicates with a number of peripheral subsystems via a bus subsystem 1202. These peripheral subsystems may include a processing acceleration unit 1206, an I/O subsystem 1208, a storage subsystem 1218 and a communications subsystem 1224. Storage subsystem 1218 includes tangible computer-readable storage media 1222 and a system memory 1210.

Bus subsystem 1202 provides a mechanism for letting the various components and subsystems of computer system 1200 communicate with each other as intended. Although bus subsystem 1202 is shown schematically as a single bus, alternative embodiments of the bus subsystem may utilize multiple buses. Bus subsystem 1202 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 1204, which can be implemented as one or more integrated circuits (e.g., a conventional microprocessor or microcontroller), controls the operation of computer system 1200. One or more processors may be included in processing unit 1204. These processors may include single core or multicore processors. In certain embodiments, processing unit 1204 may be implemented as one or more independent processing units 1232 and/or 1234 with single or multicore processors included in each processing unit. In other embodiments, processing unit 1204 may also be implemented as a quad-core processing unit formed by integrating two dual-core processors into a single chip.

In various embodiments, processing unit 1204 can execute a variety of programs in response to program code and can maintain multiple concurrently executing programs or processes. At any given time, some or all of the program code to be executed can be resident in processor(s) 1204 and/or in storage subsystem 1218. Through suitable programming, processor(s) 1204 can provide various functionalities described above. Computer system 1200 may additionally include a processing acceleration unit 1206, which can include a digital signal processor (DSP), a special-purpose processor, and/or the like.

I/O subsystem 1208 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1200 to a user or other computer. For example, user interface output devices may include, without limitation, a variety of display devices that visually convey text, graphics and audio/video information such as monitors, printers, speakers, headphones, automotive navigation systems, plotters, voice output devices, and modems.

Computer system 1200 may comprise a storage subsystem 1218 that provides a tangible non-transitory computer-readable storage medium for storing software and data constructs that provide the functionality of the embodiments described in this disclosure. The software can include programs, code modules, instructions, scripts, etc., that when executed by one or more cores or processors of processing unit 1204 provide the functionality described above. Storage subsystem 1218 may also provide a repository for storing data used in accordance with the present disclosure.

As depicted in the example in FIG. 12, storage subsystem 1218 can include various components including a system memory 1210, computer-readable storage media 1222, and a computer readable storage media reader 1220. System memory 1210 may store program instructions that are loadable and executable by processing unit 1204. System memory 1210 may also store data that is used during the execution of the instructions and/or data that is generated during the execution of the program instructions. Various different kinds of programs may be loaded into system memory 1210 including but not limited to client applications, Web browsers, mid-tier applications, relational database management systems (RDBMS), virtual machines, containers, etc.

System memory 1210 may also store an operating system 1216. Examples of operating system 1216 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, and Palm® OS operating systems. In certain implementations where computer system 1200 executes one or more virtual machines, the virtual machines along with their guest operating systems (GOSs) may be loaded into system memory 1210 and executed by one or more processors or cores of processing unit 1204.

System memory 1210 can come in different configurations depending upon the type of computer system 1200. For example, system memory 1210 may be volatile memory (such as random access memory (RAM)) and/or non-volatile memory (such as read-only memory (ROM), flash memory, etc.) Different types of RAM configurations may be provided including a static random access memory (SRAM), a dynamic random access memory (DRAM), and others. In some implementations, system memory 1210 may include a basic input/output system (BIOS) containing basic routines that help to transfer information between elements within computer system 1200, such as during start-up.

Computer-readable storage media 1222 may represent remote, local, fixed, and/or removable storage devices plus storage media for temporarily and/or more permanently containing, storing, computer-readable information for use by computer system 1200 including instructions executable by processing unit 1204 of computer system 1200.

Computer-readable storage media 1222 can include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media.

By way of example, computer-readable storage media 1222 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 1222 may include, but is not limited to, Zip® drives, flash memory cards, universal serial bus (USB) flash drives, secure digital (SD) cards, DVD disks, digital video tape, and the like. Computer-readable storage media 1222 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1200.

Machine-readable instructions executable by one or more processors or cores of processing unit 1204 may be stored on a non-transitory computer-readable storage medium. A non-transitory computer-readable storage medium can include physically tangible memory or storage devices that include volatile memory storage devices and/or non-volatile storage devices. Examples of non-transitory computer-readable storage medium include magnetic storage media (e.g., disk or tapes), optical storage media (e.g., DVDs, CDs), various types of RAM, ROM, or flash memory, hard drives, floppy drives, detachable memory drives (e.g., USB drives), or other type of storage device.

Communications subsystem 1224 provides an interface to other computer systems and networks. Communications subsystem 1224 serves as an interface for receiving data from and transmitting data to other systems from computer system 1200. For example, communications subsystem 1224 may enable computer system 1200 to connect to one or more devices via the Internet. In some embodiments communications subsystem 1224 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof)), global positioning system (GPS) receiver components, and/or other components. In some embodiments communications subsystem 1224 can provide wired network connectivity (e.g., Ethernet) in addition to or instead of a wireless interface.

In some embodiments, communications subsystem 1224 may also receive input communication in the form of structured and/or unstructured data feeds 1226, event streams 1228, event updates 1230, and the like on behalf of one or more users who may use computer system 1200.

By way of example, communications subsystem 1224 may be configured to receive data feeds 1226 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 1224 may also be configured to receive data in the form of continuous data streams, which may include event streams 1228 of real-time events and/or event updates 1230, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 1224 may also be configured to output the structured and/or unstructured data feeds 1226, event streams 1228, event updates 1230, and the like to one or more databases that may be in communication with one or more streaming data source computers coupled to computer system 1200.

Computer system 1200 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1200 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments, but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or services are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A method, comprising:

accessing a natural language utterance comprising a plurality of tokens, wherein a first token of the plurality of tokens corresponds to a first medical entity;

performing an entity analysis on the natural language utterance by:

using a first machine-learning model to assign a first class label to the first token, wherein the first class label is selected from a plurality of class labels and associated with the first medical entity, and using a second machine-learning model to link the first medical entity to a first medical code, wherein the first medical code is included in a first medical coding system that is associated with the first medical entity, wherein the first medical coding system is included in a group of medical coding systems, and wherein using the second machine-learning model to link the first medical entity to the first medical code comprises: using the second machine-learning model to associate the first medical entity with a first medical entity type of a plurality of medical entity types; and selecting the first medical coding system from the group of medical coding systems based on the first medical entity type;

generating a data structure comprising the first token, the first class label, and the first medical code; and storing the data structure in a database associated with an electronic health record (EHR) system.

2. The method of claim 1, further comprising identifying an intent from the natural language utterance.

3. The method of claim 2, wherein the identified intent is a query for medical-related information.

4. The method of claim 1, wherein each class label of the plurality of class labels corresponds to a respective medical entity type of the plurality of medical entity types.

5. The method of claim 1, wherein the first medical coding system is Systematized Nomenclature of Medicine-Clinical Terms (SNOMED CT), Prescription Normalization (RxNORM), Logical Observation Identifiers Names and Codes (LOINC), or International Classification of Diseases (ICD-10).

6. The method of claim 1, wherein the data structure is in compliance with Fast Healthcare Interoperability Resources (FHIR) standard.

7. The method of claim 1, further comprising using the data structure to generate a response to the natural language utterance.

8. The method of claim 1, further comprising assigning a higher priority to the first token of the plurality of tokens than a second token of the plurality of tokens, wherein the second token corresponds to a non-medical entity.

9. The method of claim 1, wherein the first machine-learning model is trained based on a supervised learning technique using training data including a plurality of training natural language utterances, wherein each training natural language utterance is labeled with one or more medical entities.

10. The method of claim 1, wherein the second machine-learning model is trained based on an unsupervised learning technique using training data including data structures including a plurality of medical entities, a plurality of medical entity types associated with the plurality of medical entities, and a plurality of medical code systems associated with the medical entity types.

11. One or more non-transitory computer-readable media storing instructions which, when executed by one or more processors, cause a system to perform operations comprising:

accessing a natural language utterance comprising a plurality of tokens, wherein a first token of the plurality of tokens corresponds to a first medical entity;

performing an entity analysis on the natural language utterance by:

using a first machine-learning model to assign a first class label to the first token, wherein the first class label is selected from a plurality of class labels and associated with the first medical entity, and using a second machine-learning model to link the first medical entity to a first medical code, wherein the first medical code is included in a first medical coding system that is associated with the first medical entity, wherein the first medical coding system is included in a group of medical coding systems, and wherein using the second machine-learning model to link the first medical entity to the first medical code comprises: using the second machine-learning model to associate the first medical entity with a first medical entity type of a plurality of medical entity types; and selecting the first medical coding system from the group of medical coding systems based on the first medical entity type;

generating a data structure comprising the first token, the first class label, and the first medical code; and storing the data structure in a database associated with an electronic health record (EHR) system.

12. The one or more non-transitory computer-readable media of claim 11, further comprising identifying an intent from the natural language utterance.

13. The one or more non-transitory computer-readable media of claim 12, wherein the identified intent is a query for medical-related information.

14. The one or more non-transitory computer-readable media of claim 11, wherein each class label of the plurality of class labels corresponds to a respective medical entity type of the plurality of medical entity types.

15. The one or more non-transitory computer-readable media of claim 11, wherein the first medical coding system is Systematized Nomenclature of Medicine-Clinical Terms (SNOMED CT), Prescription Normalization (RxNORM), Logical Observation Identifiers Names and Codes (LOINC), or International Classification of Diseases (ICD-10).

16. The one or more non-transitory computer-readable media of claim 11, wherein the data structure is in compliance with Fast Healthcare Interoperability Resources (FHIR) standard.

17. The one or more non-transitory computer-readable media of claim 11, further comprising using the data structure to generate a response to the natural language utterance.

18. The one or more non-transitory computer-readable media of claim 11, further comprising assigning a higher priority to the first token of the plurality of tokens than a second token of the plurality of tokens, wherein the second token corresponds to a non-medical entity.

19. The one or more non-transitory computer-readable media of claim 11, wherein the first machine-learning model is trained based on a supervised learning technique using training data including a plurality of training natural language utterances, wherein each training natural language utterance is labeled with one or more medical entities.

20. The one or more non-transitory computer-readable media of claim 11, wherein the second machine-learning model is trained based on an unsupervised learning technique using training data including data structures including a plurality of medical entities, a plurality of medical entity types associated with the plurality of medical entities, and a plurality of medical code systems associated with the medical entity types.

21. A system comprising:

one or more processing systems; and one or more computer-readable media storing instructions which, when executed by the one or more processing systems, cause the system to perform operations comprising:

accessing a natural language utterance comprising a plurality of tokens, wherein a first token of the plurality of tokens corresponds to a first medical entity;

performing an entity analysis on the natural language utterance by:

using a first machine-learning model to assign a first class label to the first token, wherein the first class label is selected from a plurality of class labels and associated with the first medical entity, and using a second machine-learning model to link the first medical entity to a first medical code, wherein the first medical code is included in a first medical coding system that is associated with the first medical entity, wherein the first medical coding system is included in a group of medical coding systems, and wherein using the second machine-learning model to link the first medical entity to the first medical code comprises: using the second machine-learning model to associate the first medical entity with a first medical entity type of a plurality of medical entity types; and selecting the first medical coding system from the group of medical coding systems based on the first medical entity type;

generating a data structure comprising the first token, the first class label, and the first medical code; and storing the data structure in a database associated with an electronic health record (EHR) system.

22. The system of claim 21, the operations further comprising identifying an intent from the natural language utterance.

23. The system of claim 22, wherein the identified intent is a query for medical-related information.

24. The system of claim 21, wherein each class label of the plurality of class labels corresponds to a respective medical entity type of the plurality of medical entity types.

25. The system of claim 21, wherein the first medical coding system is Systematized Nomenclature of Medicine-Clinical Terms (SNOMED CT), Prescription Normalization (RxNORM), Logical Observation Identifiers Names and Codes (LOINC), or International Classification of Diseases (ICD-10).

26. The system of claim 21, wherein the data structure is in compliance with Fast Healthcare Interoperability Resources (FHIR) standard.

27. The system of claim 21, further comprising using the data structure to generate a response to the natural language utterance.

28. The system of claim 21, further comprising assigning a higher priority to the first token of the plurality of tokens than a second token of the plurality of tokens, wherein the second token corresponds to a non-medical entity.

29. The system of claim 21, wherein the first machine-learning model is trained based on a supervised learning technique using training data including a plurality of training natural language utterances, wherein each training natural language utterance is labeled with one or more medical entities.

30. The system of claim 21, wherein the second machine-learning model is trained based on an unsupervised learning technique using training data including data structures including a plurality of medical entities, a plurality of medical entity types associated with the plurality of medical entities, and a plurality of medical code systems associated with the medical entity types.

* * * * *